United States Patent
Toda et al.

(10) Patent No.: US 7,499,789 B2
(45) Date of Patent: Mar. 3, 2009

(54) DETERIORATION SIGNAL GENERATION DEVICE FOR GAS SENSOR

(75) Inventors: Satoru Toda, Inazawa (JP); Kunihiko Takamatsu, Toyota (JP); Naoto Sawaki, Komaki (JP)

(73) Assignee: NGK Spark Plug Co., Ltd., Aichi (JP)

( * ) Notice: Subject to any disclaimer, the term of this patent is extended or adjusted under 35 U.S.C. 154(b) by 89 days.

(21) Appl. No.: 11/752,392

(22) Filed: May 23, 2007

(65) Prior Publication Data

US 2007/0276580 A1    Nov. 29, 2007

(30) Foreign Application Priority Data

May 24, 2006    (JP)    ............... 2006-143453

(51) Int. Cl.
*B60T 7/12*    (2006.01)
*F02D 41/14*    (2006.01)
*G01M 15/00*    (2006.01)

(52) U.S. Cl. ............... 701/109; 123/688; 60/276; 73/114.72

(58) Field of Classification Search ............... 123/688, 123/691, 692; 701/103, 108, 109, 114; 60/274, 60/276, 277; 73/114.69, 114.7, 114.71, 114.72, 73/114.73

See application file for complete search history.

(56) References Cited

U.S. PATENT DOCUMENTS

| | | | | |
|---|---|---|---|---|
| 5,154,054 A | | 10/1992 | Nakane et al. | |
| 5,235,957 A | * | 8/1993 | Furuya | 123/688 |
| 5,247,793 A | * | 9/1993 | Yamada et al. | 60/276 |
| 5,522,250 A | | 6/1996 | Gee et al. | |
| 5,526,798 A | * | 6/1996 | Seki | 123/688 |
| 5,591,905 A | * | 1/1997 | Fujimoto et al. | 73/114.75 |
| 5,927,260 A | * | 7/1999 | Kishimoto et al. | 123/688 |
| 6,176,080 B1 | | 1/2001 | Izumiura et al. | |
| 7,021,300 B2 | * | 4/2006 | Maki et al. | 123/688 |
| 7,117,664 B2 | * | 10/2006 | Takaku et al. | 60/277 |
| 7,254,474 B2 | * | 8/2007 | Iihoshi et al. | 701/109 |
| 7,387,011 B2 | * | 6/2008 | Fujiki et al. | 73/23.32 |
| 7,412,820 B2 | * | 8/2008 | Iida et al. | 60/274 |
| 7,424,801 B2 | * | 9/2008 | Mukaihira et al. | 60/277 |

FOREIGN PATENT DOCUMENTS

| | | |
|---|---|---|
| GB | 2 258 324 A | 2/1993 |
| JP | 2004-093957 A | 3/2004 |
| JP | 2004-308474 A | 11/2004 |
| JP | 2004-316569 A | 11/2004 |
| JP | 2004-316570 A | 11/2004 |

* cited by examiner

*Primary Examiner*—Willis R. Wolfe, Jr.
*Assistant Examiner*—Johnny H. Hoang
(74) *Attorney, Agent, or Firm*—Sughrue Mion, PLLC

(57) ABSTRACT

A deterioration signal generation device for a gas sensor for simulating a deterioration signal output by a gas sensor in a deteriorated state, the gas sensor detecting the fuel-air ratio of exhaust gas from an internal combustion engine based on the concentration of particular components in the exhaust gas, the deterioration signal generation device including a reference signal acquisition unit as defined herein, a reference signal storing unit as defined herein, a delay time setting unit as defined herein and a signal delay generation unit as defined herein.

9 Claims, 28 Drawing Sheets

DETERIORATION SIGNAL GENERATION DEVICE FOR GAS SENSOR

BACKGROUND OF THE INVENTION

1. Field of the Invention

The present invention relates to a deterioration signal generation device for a gas sensor which simulates a detection signal (deterioration signal) that is output by a gas sensor in a deteriorated state of the same, a gas sensor detecting the fuel-air ratio of exhaust gas from an internal combustion engine based on the concentration of particular components in the exhaust gas.

2. Description of the Related Art

Gas sensors are well-known. They are mounted in an exhaust gas passage of an internal combustion engine such as an automobile engine to detect the fuel-air ratio of the exhaust gas based on the concentration of particular components in the exhaust gas. A sensor element of such a gas sensor detects the fuel-air ratio of exhaust gas utilizing the fact that the magnitude of a current flowing the element itself or a voltage at the element undergoes binary or linear changes in accordance with the concentration of the particular element in the exhaust gas. A detection signal output from the gas sensor is transmitted to an ECU (electronic control unit), and the ECU exercises feedback control of the fuel-air ratio such as adjustment of the fuel injection amount in the engine based on the detection signal thus received.

In such a gas sensor, the sensor element is deteriorated due to aging after use for a long time because it is exposed to exhaust gas in an exhaust gas passage. Referring to the development of an ECU under the circumstances a design that allows parameters for feedback control over a fuel-air ratio to be determined optimally even for a detection signal obtained from a gas sensor in a deteriorated state is adopted such that the accuracy of feedback control over the fuel-air ratio can be maintained even when the gas sensor is deteriorated to some degree. For example, accelerated life testing is carried out to provide gas sensors at different levels of deterioration. Transient states of deterioration signals obtained from those gas sensors are predicted from the detection signals and signal detected from a normal gas sensor, whereby parameters for control are set.

When an actual vehicle is tested to check the state of cleaning of exhaust gas, a gas sensor which has been deteriorated through accelerated life testing as described above is mounted in the actual vehicle in order to check whether feedback control over the fuel-air ratio is properly exercised by an ECU even with a deteriorated gas sensor. However, it is difficult to fabricate each of gas sensors as intended through accelerated life testing such that the sensors reproduce a plurality of states of deterioration to be used for such tests. Further, it is troublesome to switch the gas sensors in different states of deterioration each time a test is conducted. Under the circumstance, deterioration signal generation devices (deterioration simulators) capable of simulating deterioration signals from gas sensors have been developed (for example, see JP-A-2004-93957).

Such a deterioration signal generation device is interposed between a normal gas sensor (in other words, a gas sensor to serve as a reference for the generation of deterioration signals) mounted in an actual vehicle and an ECU. The device processes a detection signal input to the same to simulate a deterioration signal and outputs the deterioration signal to the ECU. Specifically, a deterioration signal generation device disclosed in JP-A-2004-93957 generates a deterioration signal on a simulated basis by changing the gain of a detection signal or delaying response characteristics of the detection signal.

3. Problems to be Solved by the Invention

In most cases, a gas sensor is mounted near a cleaner that is provided downstream of an exhaust gas passage. Therefore, when a target fuel-air ratio for a mixture supplied to the internal combustion engine is changed through adjustment of the fuel injection amount, it takes some time for the mixture at the new fuel-air ratio to reach the gas sensor after being burned in the engine (combustion chamber). For this reason, there is a time lag (delay) between the timing when a change is made to the target fuel-air ratio of the mixture and the timing when a change starts appearing in a detection signal output from the gas sensor.

When a gas sensor is used for a long time, a protector of the gas sensor (which is specifically a protector with a gas communication hole covering the periphery of the sensor element) may be subjected to deterioration with time such as clogging of the gas communication hole. When the gas sensor is deteriorated as thus described, the replacement of the gas in the protector through the gas communication hole becomes slow. Thus, a detection signal from the gas sensor takes a longer time (delay time) to start changing as a result of a change in the target fuel-air ratio of the mixture when compared to a detection signal from a gas sensor which is not deteriorated. For this reason, when an ECU is developed taking deteriorated states of a gas sensor into consideration, an ECU capable of promoting more accurate feedback control over fuel-air ratio cannot be developed without paying attention to the fact that a delay time as described above changes (increases) as time passes. However, it has not been possible to simulate a deterioration signal from a gas sensor with such a delay time varied with the deterioration signal generation device disclosed in JP-A-2004-93957, although the device can simulate a deterioration signal with variable gain and response characteristics.

The invention has been made to solve the above-described problem, and it is an object of the invention to provide a deterioration signal generation device for a gas sensor which detects the fuel-air ratio of exhaust gas from an internal combustion engine based on the concentration of particular components in the exhaust gas, the device being capable of simulating a deterioration signal output by the gas sensor and outputting the deterioration signal with some delayed.

SUMMARY OF THE INVENTION (1) In order to achieve the above-described object, the invention provides a deterioration signal generation device for a gas sensor for simulating a deterioration signal output by a gas sensor in a deteriorated state, the gas sensor detecting the fuel-air ratio of exhaust gas from an internal combustion engine based on the concentration of particular components in the exhaust gas, the deterioration signal generation device including:

a reference signal acquisition unit which is connected to a reference sensor identical in configuration to the gas sensor for outputting a reference signal for generating the deterioration signal, the reference signal being associated with the concentration of the particular component in the exhaust gas, and which acquires the reference signal at constant time intervals;

a reference signal storing unit for storing the reference signals acquired by the reference signal acquisition unit in the order of acquisition;

a delay time setting unit for setting a delay time for outputting the reference signal while delaying the starting point of a change in the signal as a result of a change in a target fuel-air ratio of a mixture supplied to the internal combustion engine; and a signal delay generation unit for generating the reference signal stored in the reference signal storing unit at a time preceding the current opportunity for acquisition a number of times corresponding to the delay time set by the delay time setting unit.

(2) The invention provides a deterioration signal generation device for a gas sensor according to the item (1), in which the delay time setting unit is configured to be able to set separate types of the delay time, i.e., a rich-lean delay time for delaying the start of a change in the reference signal in the case of a change from the target fuel-air ratio from a rich side to a lean side and a lean-rich delay time for delaying the start of a change in the reference signal in the case of a change in the target fuel-air ratio from the lean side to the rich side. The signal delay generation unit includes:

a rich-lean signal delay output unit for outputting the reference signal stored in the reference signal storing unit at a time preceding the current opportunity for acquisition a number of times corresponding to the rich-lean delay time;

a lean-rich signal delay output unit for outputting the reference signal stored in the reference signal storing unit at a time preceding the current opportunity for acquisition a number of times corresponding to the lean-rich delay time; and a deterioration signal selection generation unit for generating the reference signal output from the rich-lean signal delay output unit as the deterioration signal when the value of the reference signal acquired by the reference signal acquisition unit has changed from the rich side to the lean side and generating the reference signal output from the lean-rich signal delay output unit as the deterioration signal when the value of the reference signal acquired by the reference signal acquisition unit has changed from the lean side to the rich side.

(3) The invention provides a deterioration signal generation device for a gas sensor according to the item (2), further including a fuel-air ratio change starting point detection unit for detecting a rich-lean change starting point as the starting point of a change in the reference signal as a result of a change from the target fuel-air ratio from the rich side to the lean side and a lean-rich change starting point as the starting point of a change in the reference signal as a result of a change in the target fuel-air ratio from the lean side to the rich side based on a plurality of the reference signals acquired by the reference signal acquisition unit.

The deterioration signal selection generation unit performs switching at the rich-lean change starting point such that the reference signal output from the rich-lean signal delay output unit will be generated as the deterioration signal and performs switching at the lean-rich change starting point such that the reference signal output from the lean-rich signal delay output unit will be generated as the deterioration signal.

(4) The invention provides a deterioration signal generation device for a gas sensor according to the item (3), wherein the fuel-air ratio change starting point detection unit executes a process of differentiating the reference signal and detects a differential of the reference signal exceeding a threshold for a change in the target fuel-air ratio from the rich side to the lean side as the rich-lean change starting point and a differential exceeding a threshold for a change in the target fuel-air ratio from the lean side to the rich side as the lean-rich change starting point.

(5) The invention provides a deterioration signal generation device for a gas sensor according to any of the items (1) to (4), including:

a gain factor setting unit for setting a gain factor for outputting the reference signal with the gain of the same changed; and a gain changing unit for changing the gain of the reference signal by multiplying the reference signal by the gain factor set by the gain factor setting unit.

(6) The invention provides a deterioration signal generation device for a gas sensor according to the item (5), wherein the gain factor setting unit is configured to be able to set separate types of the gain factor, i.e., a lean gain factor for changing the gain of the reference signal when the value of the reference signal is leaner than a predetermined threshold and a rich gain factor for changing the gain of the reference signal when the value of the reference signal is richer than the predetermined threshold.

The gain changing unit multiplies the reference signal by the lean gain factor when it is determined that the value of the reference signal is leaner than the predetermined threshold and multiplies the reference signal by the rich gain factor when it is determined that the value of the reference signal is richer than the predetermined threshold.

(7) The invention provides a deterioration signal generation device for a gas sensor according to any of the items (1) to (6), including:

a transition rate setting unit for setting a transition rate for outputting the reference signal with response characteristics of the signal changed, the response characteristics changing as the target fuel-air ratio changes; and a transition time changing unit for changing the response characteristics of the reference signal by multiplying the reference signal by the transition rate set by the transition rate setting unit.

(8) The invention provides a deterioration signal generation device for a gas sensor according to the item (7), wherein the transition rate setting unit is configured to be able to set separate types of the transition rate, i.e., a rich-lean transition rate for changing the response characteristics of the reference signal in the case of a change in the target fuel-air ratio from the rich side to the lean side and a lean-rich transition rate for changing the response characteristics of the reference signal in the case of a change in the target fuel-air ratio from the lean side to the rich side.

The transition time changing unit multiplies the reference signal by the rich-lean transition rate when the value of the reference signal acquired by the reference signal acquisition unit changes from the rich side to the lean side and multiplies the reference signal by the lean-rich transition rate when the value of the reference signal acquired by the reference signal acquisition unit changes from the lean side to the rich side.

(9) The invention provides a deterioration signal generation device for a gas sensor according to the item (3) or (4), including:

a holding signal storing unit for storing the deterioration signal generated at the rich-lean change starting point as a rich-lean holding signal and storing the deterioration signal generated at the lean-rich change starting point as a lean-rich holding signal; and a holding signal output unit for outputting the rich-lean holding signal as the deterioration signal when the deterioration signal generated after the rich-lean change starting point has a value greater than that of the rich-lean holding signal, the holding signal being output until the deterioration signal generated after the rich-lean change starting point becomes a value equal to or smaller than that of the rich-lean holding signal and for outputting the lean-rich holding signal as the deterioration signal when the deterioration signal generated after the lean-rich change starting point has a value smaller than that of the lean-rich holding signal, the holding signal being output until the deterioration signal generated after the lean-rich change starting point becomes a value equal to or greater than that of the lean-rich holding signal.

The deterioration signal generation device according to the item (1) can generate a deterioration signal by outputting a reference signal acquired from a reference signal with a delay of an arbitrarily set delay time. There is no need for fabricating gas sensors as intended through accelerated life testing such that the sensors reproduce a plurality of states of deterioration in which detection signal from the gas sensors start changing with different delay times as a result of a change in a target fuel-air ratio of the mixture supplied to the internal combustion engine. There is no need for developing a system (e.g., an ECU) using such gas sensors taking the different delay times as described above into consideration. That is, a deterioration signal with a delay time which can be freely changed as described above can be obtained by simply connecting a reference sensor to the deterioration signal generation device according to the invention. Therefore, a system capable of accurate feedback control of fuel-air ratio can be developed smoothly in a short time.

Detection signals may be output with different delay times when the target fuel-air ratio is changed to the rich side and when the ratio is changed to the lean side depending on the state of contamination of the gas sensor (e.g., a state of contamination attributable primarily to Pb components included in the exhaust gas or a state of contamination primarily attributable to Si components included in the exhaust gas). Under the circumstance, the use of the deterioration signal generation device according to the item (2) makes it possible to generate a deterioration signal which is output with a delay according to a lean-rich delay time when the target fuel-air ratio is changed to the rich side and to generate a deterioration signal which is output with a delay according to a rich-lean delay time when the target fuel-air ratio is changed to the lean side.

As apparent from the invention set forth in the item (3), when deterioration signals having different delay times are switched, the timing of switching is preferably determined by detecting a rich-lean change starting point at which the reference signal starts changing as a result of a change in the target fuel-air ratio to the lean side and detecting a lean-rich change starting point at which the reference signal starts changing as a result of a change in the target fuel-air ratio to the rich side.

To detect a starting point of a change in the reference signal as a result of a change in the target fuel-air ratio, as apparent from the invention set forth in the item (4), a differentiation process may be performed on the reference signal, and differentials may be compared with a threshold to identify each starting point. Thus, each starting point can be detected accurately by a simple approach.

According to the invention set forth in the item (5), a deterioration signal can be simulated from a reference signal from a reference sensor, the deterioration signal reflecting a reduction in the gain of a detection signal output by a gas sensor. Thus, the deterioration signal generation device can be provided with improved versatility. It is also possible to generate a deterioration signal having a variable delay time with the gain of the reference signal varied. Thus, a deterioration signal can be generated according to various modes of deterioration of a gas sensor.

According to the invention set forth in the item (6), a gain factor for changing the gain of a reference signal can be set at separate values, i.e., a rich gain factor for a reference signal richer than a predetermined threshold and a lean gain factor for a reference signal leaner than the same. It is therefore possible to simulate deterioration signals from a gas sensor outputting a deterioration signal only when the fuel-air ratio of exhaust gas is on the rich side and a gas sensor outputting deterioration signals at different levels of deterioration when the fuel-air ratio of exhaust gas is on the rich side and when the ratio on the lean side. Thus, deterioration signals can be generated in accordance with various modes of deterioration of gas sensors.

According to the invention set forth in the item (7), a deterioration signal reflecting a reduction in response characteristics of a signal output by a gas sensor can be simulated from a reference signal of a reference sensor. Thus, the deterioration signal generation device can be provided with improved versatility. It is also possible to generate a deterioration signal having a variable delay time with the response characteristics of the reference signal varied and to generate even a deterioration signal with the gain of the reference signal varied. Thus, a deterioration signal can be generated according to various modes of deterioration of a gas sensor.

The term "response characteristics" means the time required for a detection signal output by a gas sensor to reach a preset value after starting to change as a result of a change in a target fuel-air ratio from the rich side to the lean side of a predetermined value (which is not limited to a theoretical fuel-air ratio) or from the lean side to rich side. The time required for the change representing higher response characteristics, the shorter it is (the quicker the change proceeds).

According to the invention set forth in the item (8), a transition rate for changing response characteristics of a reference signal can be set at separate values, i.e., a lean-rich transition rate for changing the response characteristics of the reference signal when the target fuel-air ratio is changed from the lean side to the rich side and a rich-lean transition rate for changing the response characteristics of the reference signal when the target fuel-air ratio is changed from the rich side to the lean side. It is therefore possible to simulate deterioration signals from a gas sensor outputting a deterioration signal only when the target fuel-air ratio is changed from the rich side to the lean side and a gas sensor outputting deterioration signals at different levels of deterioration. Thus, deterioration signals can be generated in accordance with various modes of deterioration of gas sensors.

Referring to reference signals from which deterioration signals are generated, switching takes place at a lean-rich change starting point from a reference signal output by a lean-rich signal delay output unit to a reference signal output by a rich-lean signal delay output unit. At this time, if the value of the reference signal output by the rich-lean signal delay output unit is greater than the value of the reference signal output by the lean-rich signal delay output unit, the value of a deterioration signal thus generated can temporarily increase at the rich-lean change starting point from a falling state and the signal value can thereafter fall. That is, the signal can change in a wavy manner, Under the circumstance, according to the invention set forth in the item (9), a rich-lean holding signal is substituted for a deterioration signal generated by the rich-lean signal delay output unit on and after a rich-lean change starting point. As a result, the value of the deterioration signal changes from a falling state to a constant state and then enters a falling state again, whereby the signal can be prevented from changing in a wavy manner. A lean-rich holding signal may similarly be substituted for a deterioration signal output by the lean-rich signal delay output unit on and after a lean-rich change starting point, which makes it possible to prevent the value of a resultant deterioration signal from changing in a wavy manner. Thus, there will be no risk of problems such as signal abnormalities when a deterioration signal output by the deterioration signal generation device is used for a secondary purpose.

DESCRIPTION OF REFERENCE NUMERALS

Figure 1:
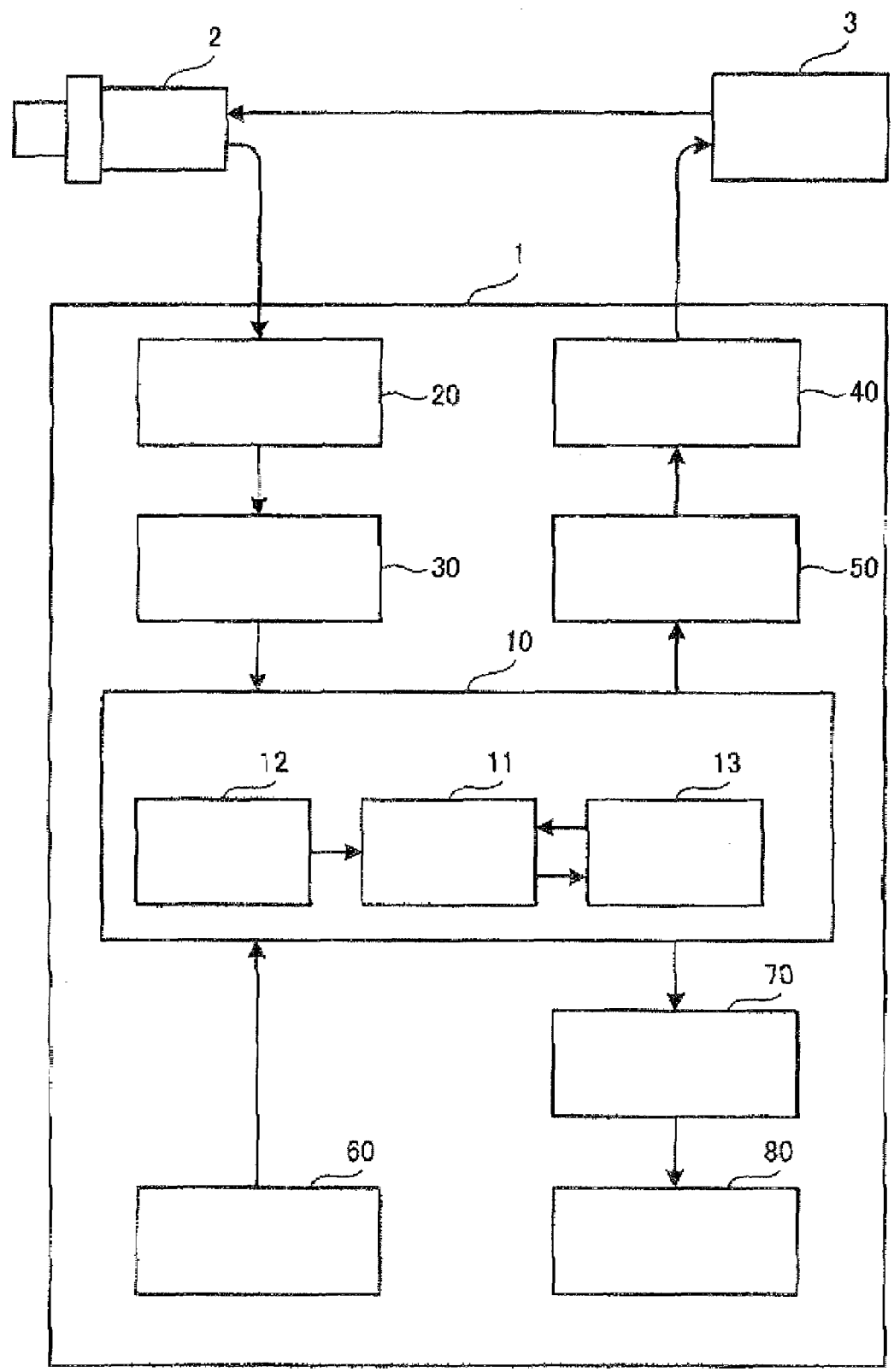
FIG. 1 is a block diagram showing a schematic configuration of a sensor simulator 1 as an example of a deterioration signal generator in a mode for carrying out the invention.

Reference numerals used to identify various structural features in the drawings include the following.
1: sensor simulator
2: reference sensor
11: CPU
12: EEPROM
13: RAM
60: input unit
121: set value storage area
132: variable storage area
Vin: reference signal
Vout: deterioration signal
RichDelayTime: lean-rich delay time
LeanDelayTime: rich-lean delay time
Du: differential
UpThreshold: threshold used when fuel-air ratio is changed from lean side to rich side
DownThreshold: threshold used when fuel-air ratio is changed from rich side to lean side
RichGain: rich gain rate
LeanGain: lean gain rate
GainThreshold: threshold
RichTimeConstant: lean-rich transition rate
LeanTimeConstant: rich-lean transition rate
Vbase: rich-lean holding signal, lean-rich holding signal

DETAILED DESCRIPTION OF THE INVENTION

A specific embodiment of a deterioration signal generator according to the invention will now be described with reference to the drawings. FIG. 1 is a block diagram showing a schematic configuration of a sensor simulator 1 as an example of a deterioration signal generator in the present mode for carrying out the invention. An oxygen sensor, a universal fuel-air ratio sensor, or a NOx sensor may be used as a gas sensor to be connected to the deterioration signal generator according to the invention. In the present embodiment, a λ-type oxygen sensor is used as an example of such sensors, and the description will be made on an assumption that a normal λ-type oxygen sensor (which is not deteriorated) is used as a reference sensor 2. While the details of the λ-type oxygen sensor used will not be described because it is a well-known type, the description is specifically based on an assumption that a cylindrical oxygen sensor as disclosed in JP-A-2004-138599 is used.

As shown in FIG. 1, the sensor simulator 1 is a device interposed between the reference sensor 2 that is an oxygen sensor mounted in an exhaust path (not shown) of an automobile and an ECU 3 exercising electronic control over the automobile. The reference sensor 2 outputs a detection signal according to the concentration of oxygen in an exhaust gas flowing through the exhaust path, and the detection signal is input to the sensor simulator 1 as a reference signal. The sensor simulator 1 processes the input reference signal by executing a deterioration signal generation program to be described later to generate a deterioration signal and outputs the signal to the ECU 3. Based on the input deterioration signal, the ECU 3 exercises control over the engine which is not shown (e.g., the adjustment of the injection amount and injection timing of fuel injected by the injector and the adjustment of ignition timing). The ECU 3 also supplies a heater driving voltage to a heater circuit (not shown) of the reference sensor 2 to activate a sensor element (not shown) quickly and to stabilize the same after activation.

The sensor simulator 1 includes a microcomputer 10 provided in a casing which is not shown, the microcomputer having a CPU 11 which controls the microcomputer itself a rewritable EEPROM 12 in which the deterioration signal generation program to be described later is stored, and a RAM 13 in which various data are temporarily stored. The CPU 11, the EEPROM 12, and the RAM 13 of the microcomputer 10 have well-known configurations. The configurations of storages areas of the EEPROM 12 and the RAM 13 will be described later.

Connected to the microcomputer 10 are an A-D converter 30 for performing A-D conversion of the reference signal input from the reference sensor 2 through an input interface 20 and a D-A converter 50 for performing D-A conversion of a deterioration signal generated by the deterioration signal generation program to be described later to output the same to the ECU 3 through an output buffer 40. An input unit 60 for allowing a user to input set values to be used for the deterioration signal generation program and a display control unit 70 for exercising display control over a display unit 80 for displaying the input set values to allow verification of the same are further connected to the microcomputer 10. For example, a push-switch or rotary switch is used as the input unit 60, and an LCD display is used as the display unit 80. Although not shown, the sensor simulator 1 also includes a power supply circuit.

The deterioration signal generation program to be described later executes a multiplicity of processes on a sub-routine basis in generating a deterioration signal from the reference signal, and various intermediate signals are generated during the processes. In the deterioration signal generation program, intermediate signals are exchanged between the subroutines using a multiplicity of variables stored in a variable storage area 132 of the RAM 13. In the present embodiment, a process of storing an intermediate signal which has been processed in one subroutine as a variable may be referred to as "output" for the sake of convenience, and a process of reading the intermediate signal stored as a variable into another subroutine may be referred to as "input" for the sake of convenience.

Figure 2:
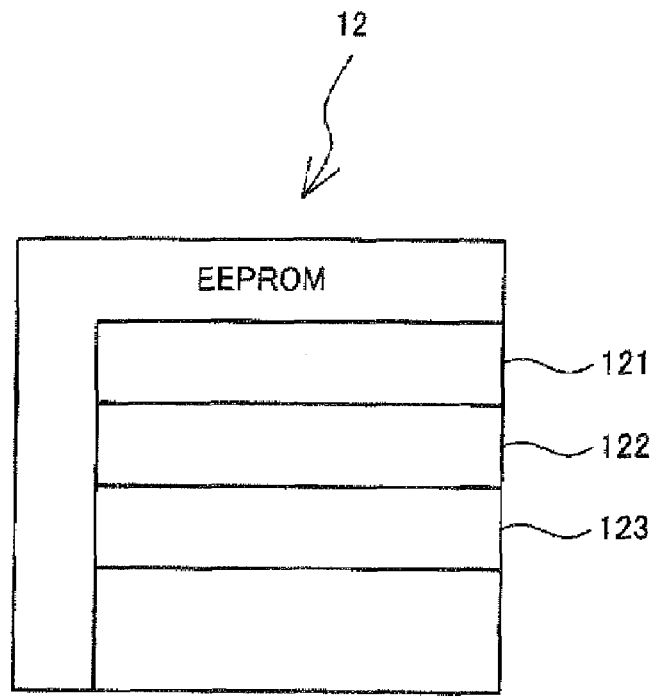
FIG. 2 is a conceptual illustration of a configuration of storage areas of an EEPROM 12.
Figure 3:
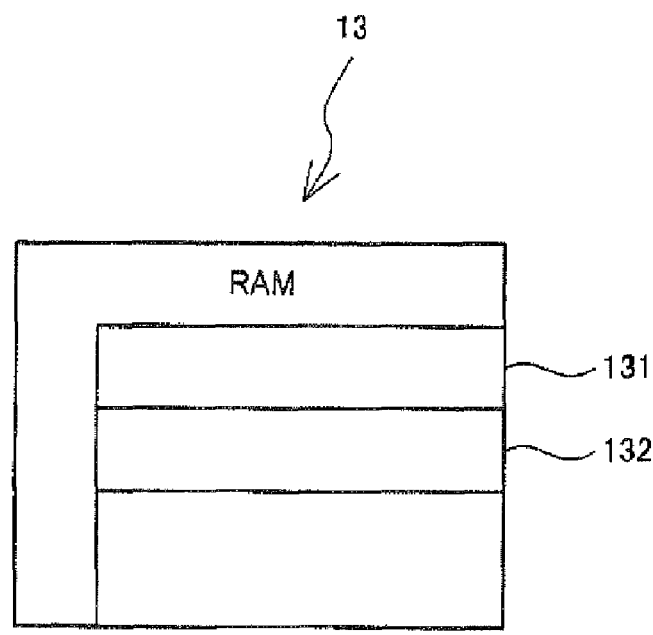
FIG. 3 is a conceptual illustration of a configuration of storage areas of a RAM 13.

Schematic configurations of storage areas of the EEPROM 12 and storage areas of the RAM 13 will now be described with reference to FIGS. 2 and 3. FIG. 2 is a conceptual illustration of a configuration of the storage areas of the EEPROM 12. FIG. 3 is a conceptual illustration of a configuration of the storage areas of the RAM 13.

As shown in FIG. 2, a set value storage area 121, a program storage area 122, and an initial value storage area 123 are provided in the EEPROM 12. In the set value storage area 121, set values of seven variables to be described later (Rich-Gain, LeanGain, GainThreshold, RichTimeConstant, LeanTimeConstant, RichDelayTime, and LeanDelayTime) are stored and are used by the deterioration signal generation program. A user inputs arbitrary values from the input unit 60 as the set values which are then stored in the EEPROM 12, and the values can therefore be saved even when the power supply is disconnected. The deterioration signal generation program is stored in the program storage area 122. The use of the EEPROM 12 realizes a configuration having flexibility to accommodate upgrading. Further, the EEPROM 12 is provided with various storage areas which are not shown.

As shown in FIG. 3, a work area 131 and a variable storage area 132 are provided in the RAM 13. The work area 131 is a storage area into which the deterioration signal generation program is read and expanded, and the area is used for the execution of the program. Various variables and count values as described below are stored in the variable storage area 132 and are used when the deterioration signal generation program is executed.

A description will now be made on variables and count values used by the deterioration signal generation program. "Vin" represents a variable for storing the voltage of the reference signal acquired from the reference sensor 2, and the initial value of the variable is set at 0. "GainThreshold" represents a variable for storing a threshold for determining on which of the rich side and the lean side the fuel-air ratio of exhaust gas resides from the voltage of the reference signal, and a value prescribed by a user in advance is set as the initial value of the variable. "RichGain" represents a variable for storing a gain factor by which the voltage of the reference signal is to be multiplied to obtain a first intermediate signal (a voltage Vint1) when the fuel-air ratio of exhaust gas is on the rich side, and a value prescribed by a user is set as the initial value of the variable. "LeanGain" represents a variable for storing a gain factor by which the voltage of the reference signal is to be multiplied to obtain the first intermediate signal (the voltage Vint1) when the fuel-air ratio of exhaust gas is on the lean side, and a value prescribed by a user is set as the initial value of the variable. "Vint1" represents a variable for storing the voltage of the first intermediate signal which is obtained by changing the gain of the voltage Vin of the reference signal, and the initial value of the variable is set at 0.

"prevVin" represents a variable for storing and saving the voltage Vin of the latest reference signal acquired and for using the same for the next operation (1 ms later), and the initial value of the variable is set at 0. "Vdiff" is a variable for storing a differential of the reference signal, and the differential is obtained as an approximate value of a difference between the voltage prevVin of the previously acquired reference signal and the voltage Vin of the last reference signal acquired, and the initial value of the variable is set at 0. "prevVdiff[i]" represents 99 variables for storing differentials from a differential prevVdiff[99] calculated at the 99th latest opportunity up to a differential prevVdiff[1] calculated previously, and 0 is stored as the initial value of each of the variables. "VdiffSum" represents a variable for storing the sum of the differentials from the differential prevVdiff[99] calculated at the 99th latest opportunity up to the differential prevVdiff[1] calculated previously and a differential Vdiff calculated latest, and the initial value of this variable is set at 0. "i" is a variable for specifying storage areas for the differentials prevVdiff[i] and storage areas for voltages prevVint3[i] which will be described later, and the initial value of this variable is set at 1. "du" is a variable for storing an average value of 100 differentials from the differential of the reference signal acquired at the 99th latest opportunity (99 ms ago) up to the differential of the reference signal acquired latest, and the initial value of this variable is set at 0.

"StepCount" represents a count value for measuring the lapse of one second to obtain an upward peak value tmpUpPeak and a downward peak value tmpDownPeak in one second, and the initial value of the variable is set at 0. "tmpUpPeak" represents a variable for storing an upward peak value that is the maximum value of an average differential du in the last one second, and the initial value of the variable is set at 0. "tmpDownPeak" represents a variable for storing a downward peak value that is the minimum value of the average differential du in the last one second, and the initial value of the variable is set at 0. "prevUpPeak1" represents a variable for storing the upward peak value in one second obtained previously (one second ago), and the initial value of the variable is set at 0. "prevUpPeak2" represents a variable for storing the upward peak value in one second obtained the time before last (two seconds ago), and the initial value of the variable is set at 0. "prevDownPeak1" represents a variable for storing the downward peak value in one second obtained previously (one second ago), and the initial value of the variable is set at 0. "prevDownPeak2" represents a variable for storing the downward peak value in one second obtained the time before last (two seconds ago), and the initial value of the variable is set at 0. "UpPeak" represents a variable for storing an average value of the upward peak values (tmpUpPeak, prevUpPeak1, prevUpPeak2) at the last three acquisitions (in the last three seconds), and the initial value of the variable is set at 0.005. "DownPeak" represents a variable for storing an average value of the downward peak values (tmpDownPeak, prevDownPeak1, prevDownPeak2) at the last three acquisitions (in the last three seconds), and the initial value of the variable is set at −0.005. "UpThreshold" is a variable for storing a threshold which is compared with the average value du indicating changes in the reference signal to detect that the fuel-air ratio of exhaust gas has been changed from the lean side to the rich side. A value that is 0.15 times the variable UpPeak is calculated and stored as this variable. "DownThreshold" is a variable for storing a threshold which is compared with the average value du indicating changes in the reference signal to detect that the fuel-air ratio of exhaust gas has been changed from the rich side to the lean side. A value that is 0.15 times the variable DownPeak is calculated and stored as this variable.

"state" represents a flag indicating the state of the fuel-air ratio of exhaust gas, and −1 is stored to indicate a state in which a change in the reference signal has been detected as a result of a change in a target fuel-air ratio of a mixture supplied to the engine (not shown) from the rich side to the lean side (hereinafter referred to as "falling state"). On the contrary, 1 is stored to indicate a state in which a change in the reference signal has been detected as a result of a change in the target fuel-air ratio from the lean side to the rich side (hereinafter referred to as "rising state"). "prevState1" represents a flag for storing the value of the state flag determined previously (1 ms ago) in order to use the value for a threshold check process.

"RichTimeConstant" represents a variable for storing a lean-rich transition rate used for changing response characteristics of the reference signal (which is the first intermediate signal in the present embodiment) in the state in which a change in the fuel-air ratio from the lean side to the rich side has been detected as a result of a change in the reference signal, and the initial value of the variable is set at 0. "LeanTimeConstant" represents a variable for storing a rich-lean transition rate used for changing response characteristics of the reference signal (which is the first intermediate signal in the present embodiment) in the state in which a change in the fuel-air ratio from the rich side to the lean side has been detected as a result of a change in the reference signal, and the initial value of the variable is set at 0. "α" represents a coefficient used in an expression for changing the response characteristics of the reference signal (which is the first intermediate signal in the present embodiment), and a value calculated using the above-described transition rate is stored. "Vint2" represents a variable for storing the voltage of a second intermediate signal obtained by changing the response characteristics of the reference signal (which is the first intermediate signal in the present embodiment), and the initial value of the variable is set at 0. "prevVint2" represents a variable for storing and saving the voltage Vint2 of the second intermediate signal obtained as a result the execution of the latest response characteristics processing and for using the same for the next operation (1 ms later), and the initial value of the variable is set at 0.

"prevState2" represents a flag which is stored to save the value of the "state" flag determined previously (1 ms ago) and to use the value in a first overshoot check process. "Vbase" represents a variable for storing a correction voltage for correcting the voltage Vint2 of the second intermediate signal in the first overshoot check process. The correction is made such that no wavy change occurs during the transition of the voltage Vin of the reference signal as a result of a change in the target fuel-air ratio when the changing direction of the voltage is temporarily reversed (e.g., a change from high potential to low potential is reversed into a change from low potential to high potential) as the transition rate is changed during the response characteristic processing. The variable is similarly used in a second overshoot check process to store a correction voltage for correcting a voltage Vout of an output deterioration signal, and the initial value of the variable is set at 0. "CheekFlag" represents a flag where 1 is stored when it is required to correct voltages using the variable "Vbase" in the first overshoot check process and the second overshoot check process, and the initial value of the flag is set at 0. "Vint3" represents a variable for storing the voltage of a third intermediate signal which is generated by correcting the voltage Vint2 of the second intermediate signal at the first overshoot cheek process, and the initial value of the variable is set at 0.

"prevVint3[i]" (i=0, 1, 2, . . . , 600) represents 601 variables for storing and saving the voltages Vint3 of the third intermediate signal obtained once per millisecond during the last 600 ms through the response characteristic processing and the first overshoot check process and for outputting the voltages at timing delayed by a delay time (RichDelayTime or LeanDelayTime) at a delaying process. Each of the variables is set at an initial value of 0. "RichDelayTime" represents a variable for storing a lean-rich delay time which is used for outputting the reference signal (which is the third intermediate signal in the present embodiment) with a delay ranging from 0 to 600 ms in the state in which a change in the fuel-air ratio from the lean side to the rich side attributable to a change in the reference signal has been detected. The initial value of the variable is set at 0. "LeanDelayTime" represents a variable for storing a rich-lean delay time which is used for outputting the reference signal (which is the third intermediate signal in the present embodiment) with a delay ranging from 0 to 600 ms in the state in which a change in the fuel-air ratio from the rich side to the lean side attributable to a change in the reference signal has been detected. The initial value of the variable is set at 0. "prevState3" represents a flag which is stored to save the value of the state flag determined previously (1 ms ago) and to use it in the second overshoot check process.

"Vint4" represents a variable for storing the voltage of a fourth intermediate signal obtained by outputting the third intermediate signal with a delay of [RichDelayTime] ms in the state in which a change in the fuel-air ratio from the lean side to the rich side attributable to a change in the reference signal has been detected. The initial value of the variable is set at 0. "Vint5" represents a variable for storing the voltage of a fifth intermediate signal obtained by outputting the third intermediate signal with a delay of [LeanDelayTime] ms in the state in which a change in the fuel-air ratio from the rich side to the lean side attributable to a change in the reference signal has been detected. The initial value of the variable is set at 0. "prevVint5" represents a variable for storing and holding the voltage Vint5 of the fifth intermediate signal which has been selected as a deterioration signal previously (1 ms ago), and the initial value of the variable is set at 0. "tVout" represents a variable for storing the voltage of a deterioration signal generated from the reference signal as a result of the execution of the deterioration signal generation program, and 0 is stored as the initial value of the variable. Further, the RAM 13 is provided with various storage areas which are not shown.

Figure 4:
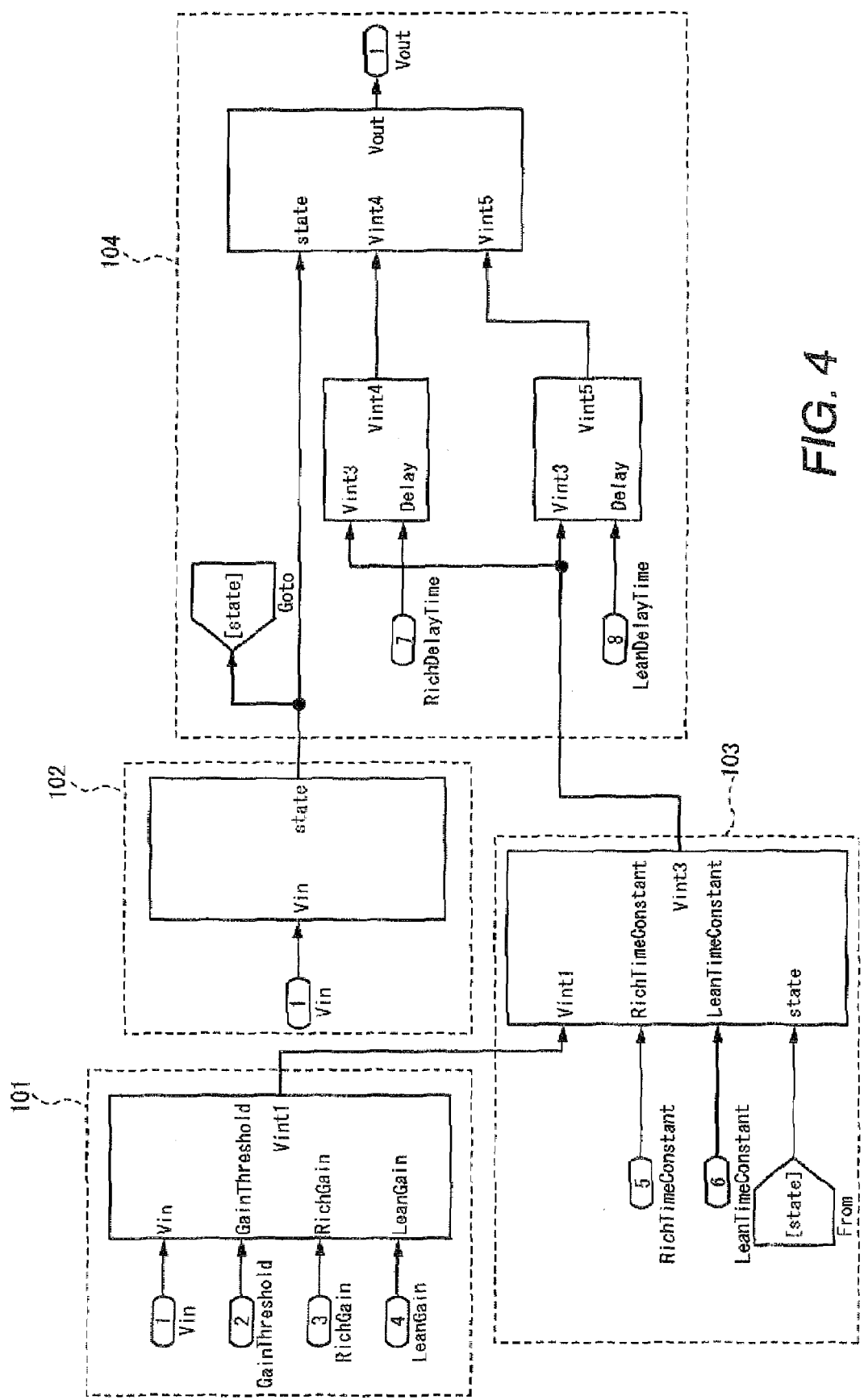
FIG. 4 is a flow block diagram for explaining a general flow of operations of a deterioration signal generation program.

The sensor simulator 1 having such a configuration acquires the reference signal one per millisecond from the reference sensor 2, processes the reference signal to generate a deterioration signal, and outputs the same to the ECU 3 in accordance with the execution of the deterioration signal generation program shown in the flow charts in FIGS. 5 to 18 which will be described later Prior to detailed description of the deterioration signal generation program, a brief description will be made on operations F of the deterioration signal generation program with reference to the flow block diagram shown in FIG. 4. FIG. 4 is a flow block diagram for explaining a general flow of operations of the deterioration signal generation program.

As shown in FIG. 4, the deterioration signal generation program is constituted by four processing blocks, i.e., a gain processing block 101, a rise/fall detection block 102, a response characteristics processing block 103, and a delaying process block 104.

The gain processing block 101 performs a process of changing (amplifying or attenuating) the gain of the reference signal (voltage Vin) input thereto. The voltage Vin is amplified or attenuated with different gain factors RichGain and LeanGain depending on whether it is greater or smaller than a predetermined threshold GainThreshold. The first intermediate signal (voltage Vint1) obtained by amplifying or attenuating the reference signal (voltage Vin) is output to the response characteristics processing block. The gain processing block 101 corresponds to a gain process (S3) in the flow chart of the deterioration signal generation program to be described later (see FIG. 5).

The rise/fall detection block 102 performs a process of detecting a starting point at which the reference signal (voltage Vin) from the reference sensor 2 start changing as a result of a change in a target fuel-air ratio from a rich state to a lean state or from the lean state to the rich state. The value of the above-deseribed "state" flag is determined based on the result of a differentiation process performed on the input reference signal (voltage Vin). The value of the "state" flag is maintained until the next change in the reference signal is detected as a result of a change in the target fuel-air ratio. That is, the timing at which the value of the "state" flag changes constitutes the above-described starting point. The rise/fall detection block 102 corresponds to a moving average calculation process (S5) for obtaining the differential du of the reference signal, a peak value detection process (S6) for obtaining thresholds UpPeak and DownPeak, and a threshold check process (S7) in the flow chart of the deterioration signal generation program to be described later (see FIG. 5).

The response characteristics processing block 103 performs a process of changing the response characteristics of the first intermediate signal (voltage Vint1) whose gain has been changed by the gain processing block 101. When the target fuel-air ratio is changed from the rich side to the lean side, the voltage changes from a voltage output by the oxygen sensor in a stable state on the rich side to a voltage output by the oxygen sensor in a stable state on the lean side. The description similarly applies to the case in which the target fuel-air ratio is changed from the lean side to the rich side. The term "response characteristics" used in the present embodiment means the time that a voltage takes to reach a predetermined value after it starts changing (the speed of change) as a result of a change in the target fuel-air ratio. Response characteristics are higher, the shorter the time required for the change (the quicker the change). Therefore, when the oxygen sensor is deteriorated, response characteristics are degraded, and a change in a voltage takes a longer time.

The response characteristics processing block 103 obtains the second intermediate signal (voltage Vint2) by changing the response characteristics of the first intermediate signal (voltage Vint1) obtained by the gain processing block 101 using Expression 1 shown below.

$$\text{Vint2}=(1-\alpha)\times \text{Vint1}+\alpha\times \text{prevVint2} \qquad \text{Expression 1}$$

where prevVint2 represents the value of voltage Vint2 calculated at the time of previous sampling.

The lean-rich transition rate RichTimeConstant and the rich-lean transition rate LeanTimeConstant are used in order to allow response characteristics to be changed by using different transition rates in the rising and falling states, and the coefficient α is calculated using Expressions 2 and 3 shown below.

In the state in which a change in the reference signal has been detected as a result of a change in the target fuel-air ratio from the lean side to the rich side (rising state);

$$\alpha=\exp\{-1/(1+\text{RichTimeConstant}/Ts)\} \qquad \text{Expression 2}$$

In the state in which a change in the reference signal has been detected as a result of a change in the target fuel-air ratio from the rich side to the lean side (falling state);

$$\alpha=\exp\{-1/(1+\text{LeanTimeConstant}/Ts)\} \qquad \text{Expression 3}$$

Ts represents a sampling interval which is 1 ms in the present embodiment.

The response characteristics processing block 103 further performs the first overshoot check process. For example, when the target fuel-air ratio is changed from the rich side to the lean side, a voltage output by the λ-type oxygen sensor will change from high potential to low potential. At this time, as a result of the execution of the response characteristics changing process, the voltage may temporarily change from low potential to high potential (the direction of change is reversed), and the change may therefore take a wavy form. The overshoot check process is a process of correcting the third intermediate signal (voltage Vint3) as a final output signal such that no temporary reversal occurs in the changing direction of the same. The response characteristics processing block 103 corresponds to response characteristics processing (S9) and a first overshoot check process (S10) in the flow chart of the deterioration signal generation program to be described later (see FIG. 5).

Next, the delaying process block 104 performs of changing the delay time of the third intermediate signal (voltage Vint3)

whose response characteristics have been changed by the response characteristics processing block 103 to output the resultant signal as a deterioration signal (voltage Vout). In this processing block, a set of the voltages Vint3 of the third intermediate signal area stored and saved starting with the voltage input 600 ms ago and up to the voltage Vint3 input this time. When the state of the fuel-air ratio is on the rich side (in the rising state), the third intermediate signals (voltages Vint3) which have been input before the lapse of the delay time specified by the lean-rich delay time RichDelayTime are generated as the fourth intermediate signals (voltages Vint4). Similarly, when the state of the fuel-air ratio is on the lean side (in the falling state), the third intermediate signals (voltages Vint3) which have been input before the lapse of the delay time specified by the rich-lean delay time LeanDelayTime are generated as the fifth intermediate signals (voltages Vint5).

Further, the second overshoot check process is performed to correct the fourth intermediate signals (voltages Vint4) in the rising state and to correct the fifth intermediate signals (voltages Vint5) in the falling state in a manner similar to the first overshoot check process described above, whereby a deterioration signal (voltage Vout) is generated and output. The delaying process block 104 corresponds to a delaying process (S11) and a second overshoot check process (S13) in the deterioration signal generation program to be described later (see FIG. 5).

As thus described, steps of generating a deterioration signal by processing a reference signal at each processing block are realized by the deterioration signal generation program in the present embodiment. A description will now be made according to the flow charts shown in FIGS. 5 to 18 and with reference to the graphs in FIGS. 19 to 30 on the steps for processing a reference signal into a deterioration signal by executing the deterioration signal generation program.

Figure 5:
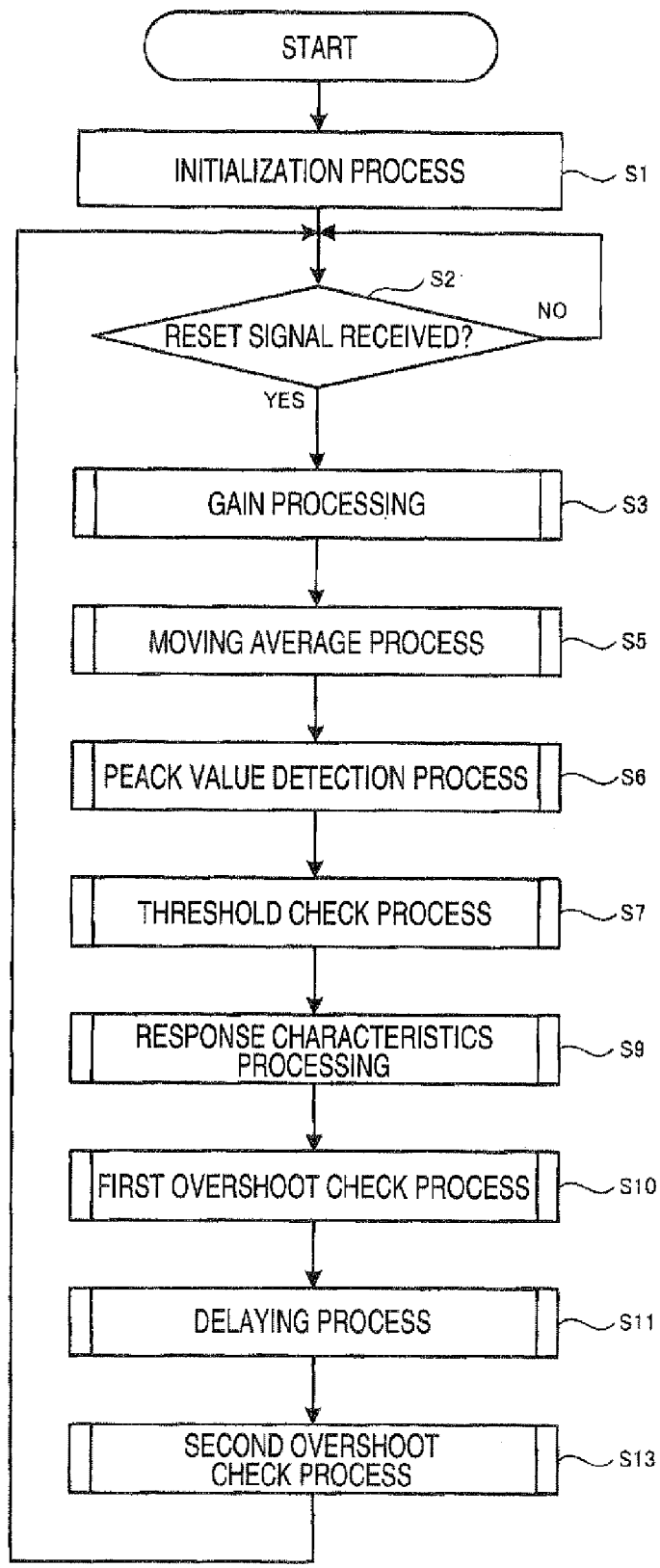
FIG. 5 is a flow chart showing a main routine of the deterioration signal generation program.
Figure 6:
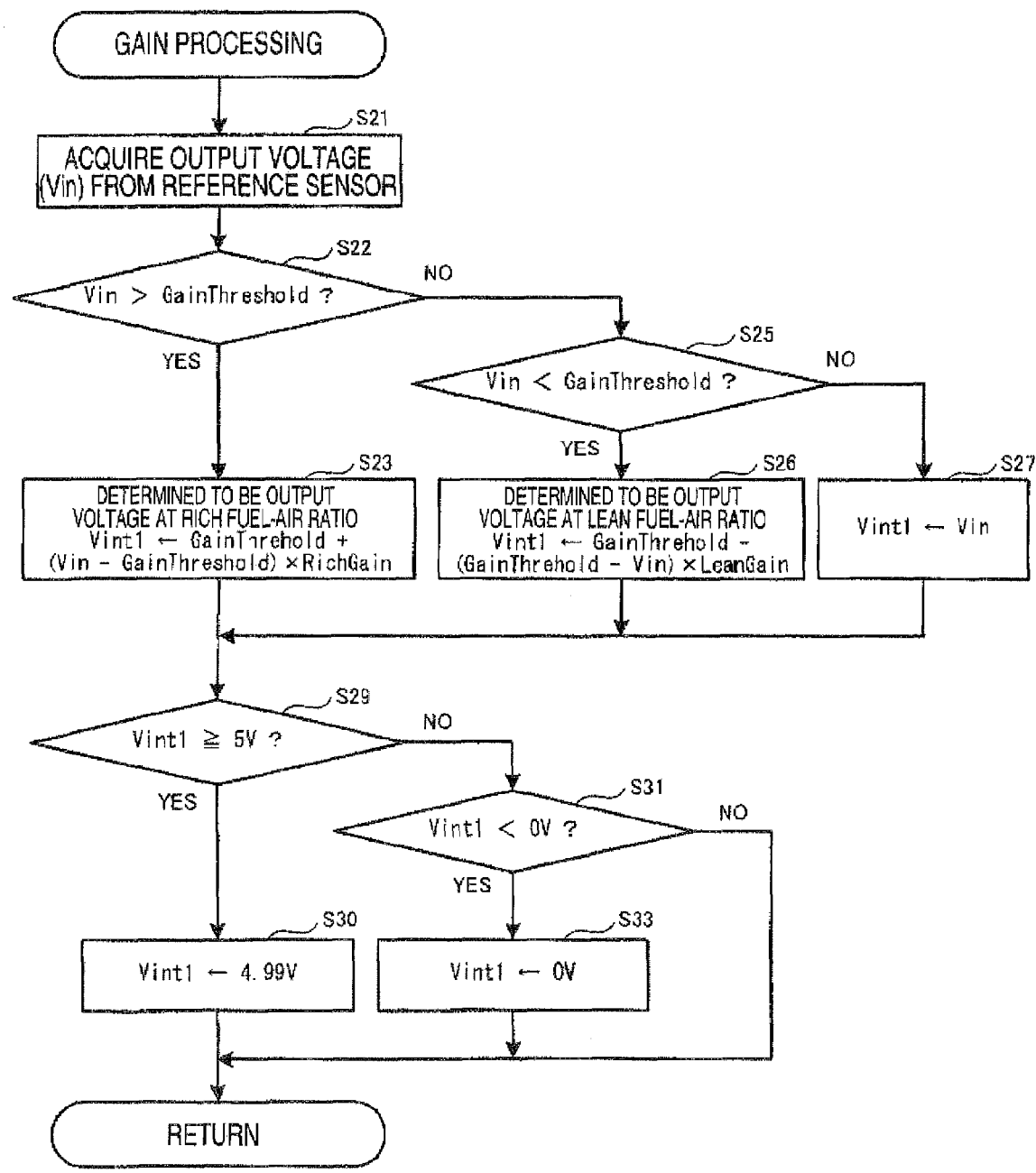
FIG. 6 is a flow chart of a gain processing subroutine.
Figure 7:
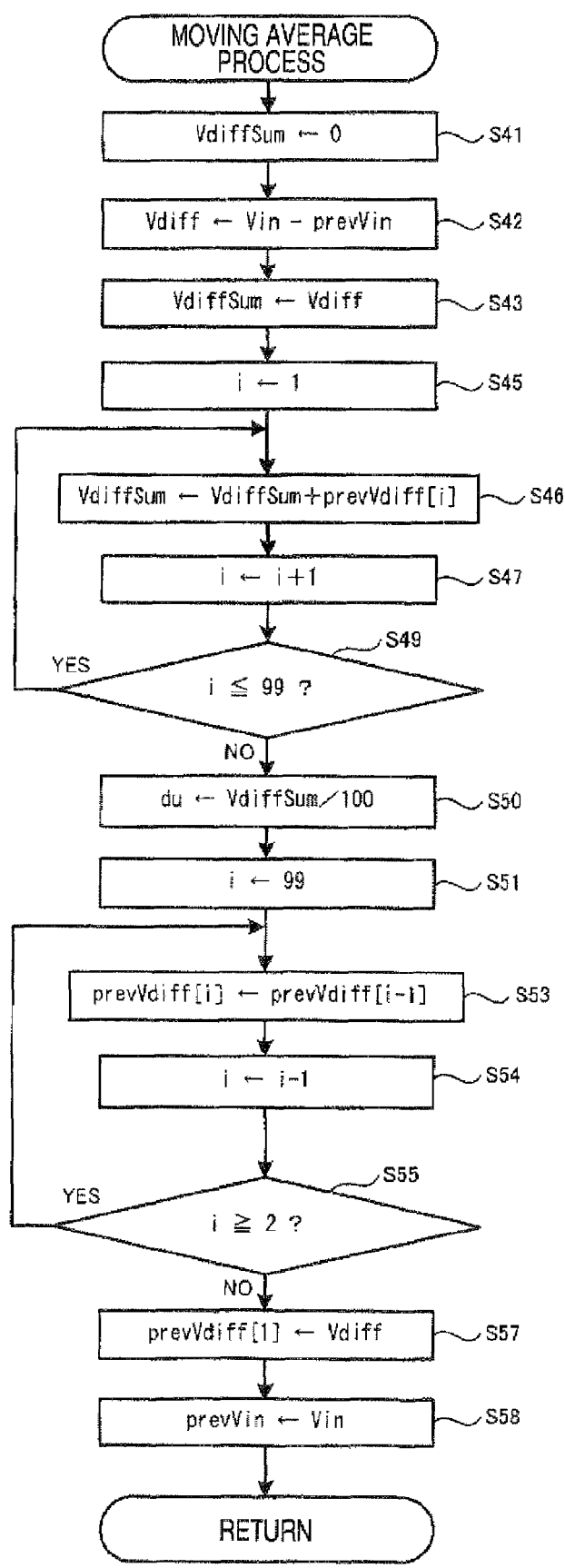
FIG. 7 is a flow chart of a moving average process subroutine.
Figure 8:
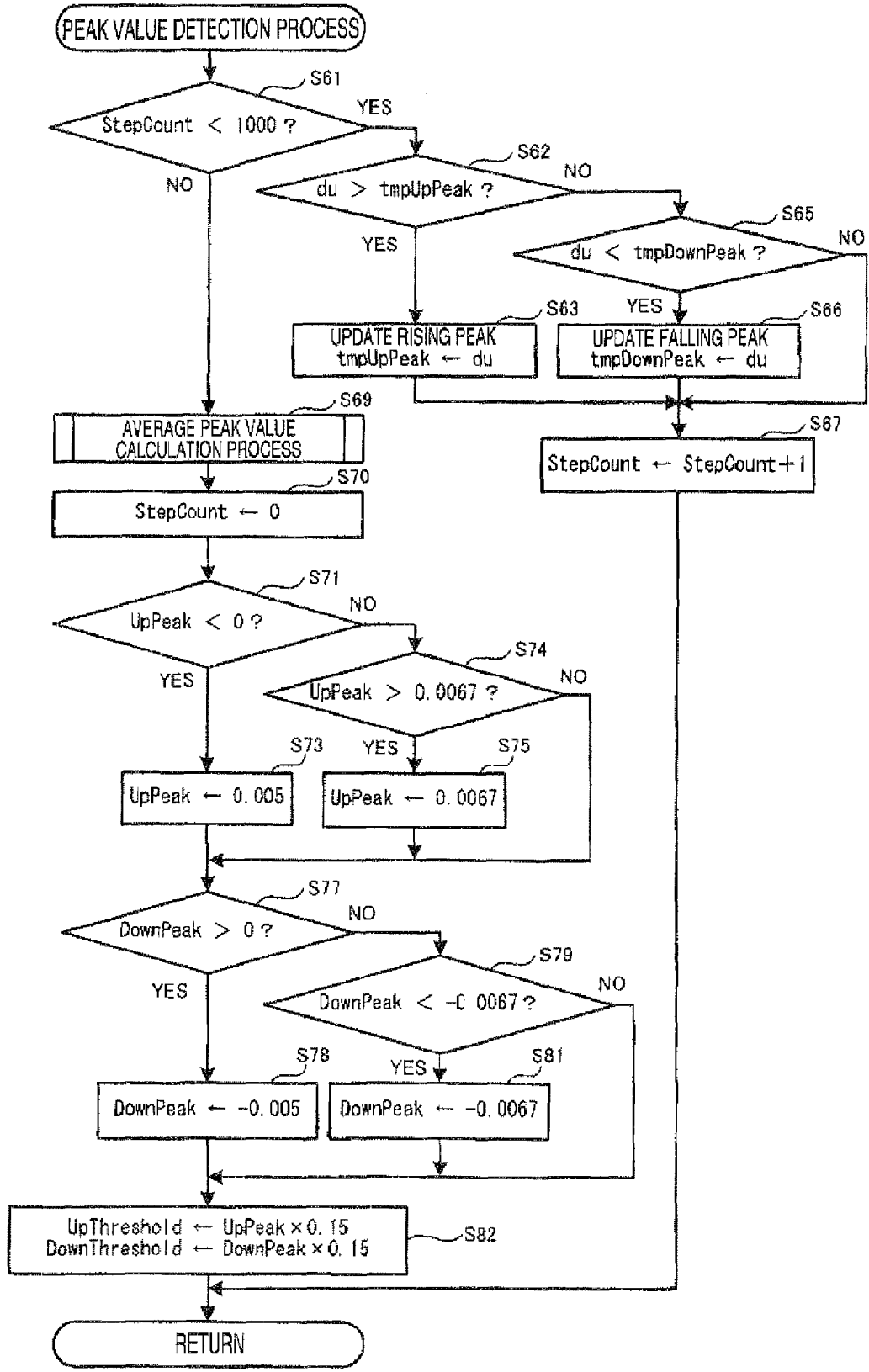
FIG. 8 is a flow chart of a peak detection process subroutine.
Figure 9:
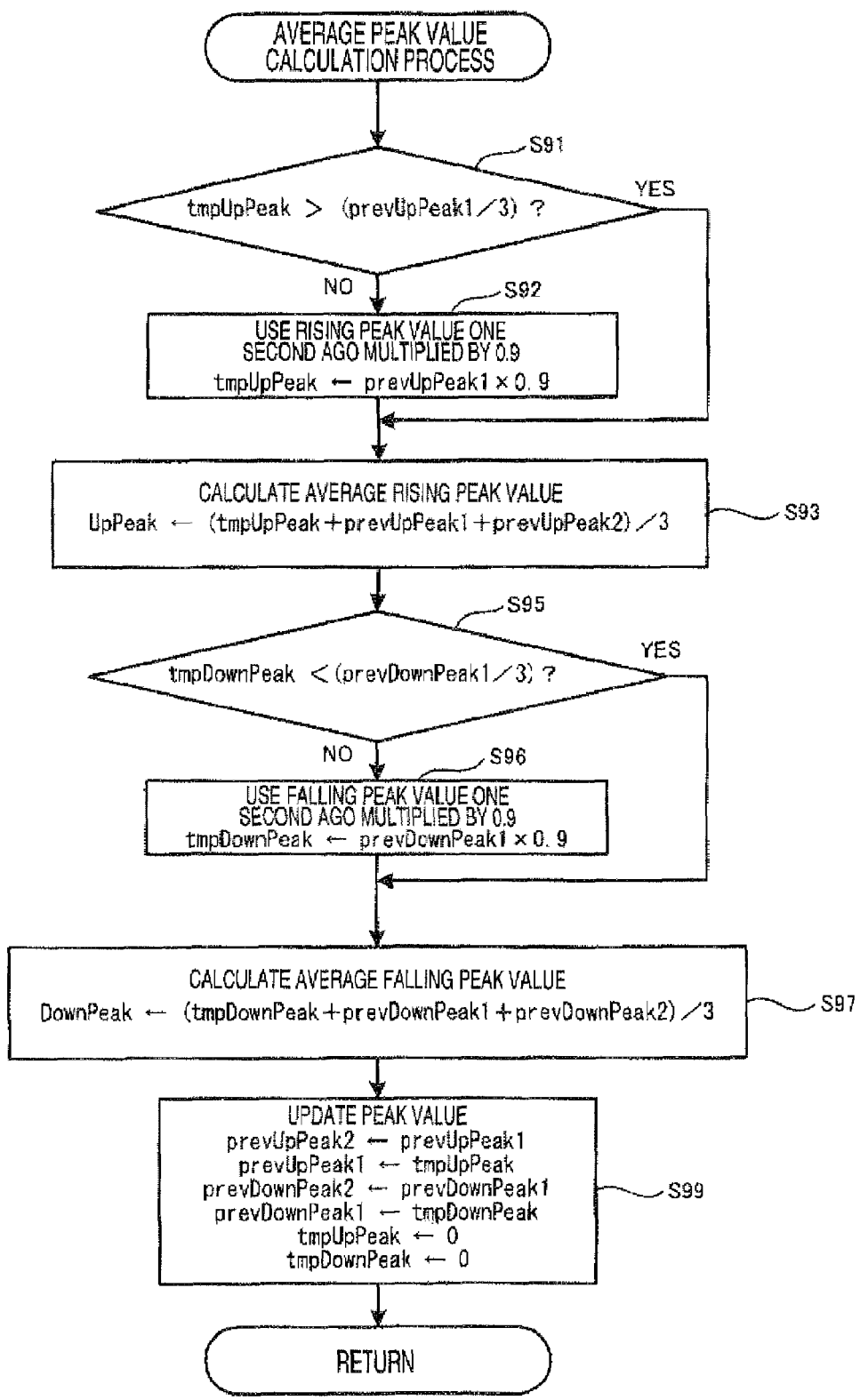
FIG. 9 is a flow chart of an average peak value calculation process subroutine.
Figure 10:
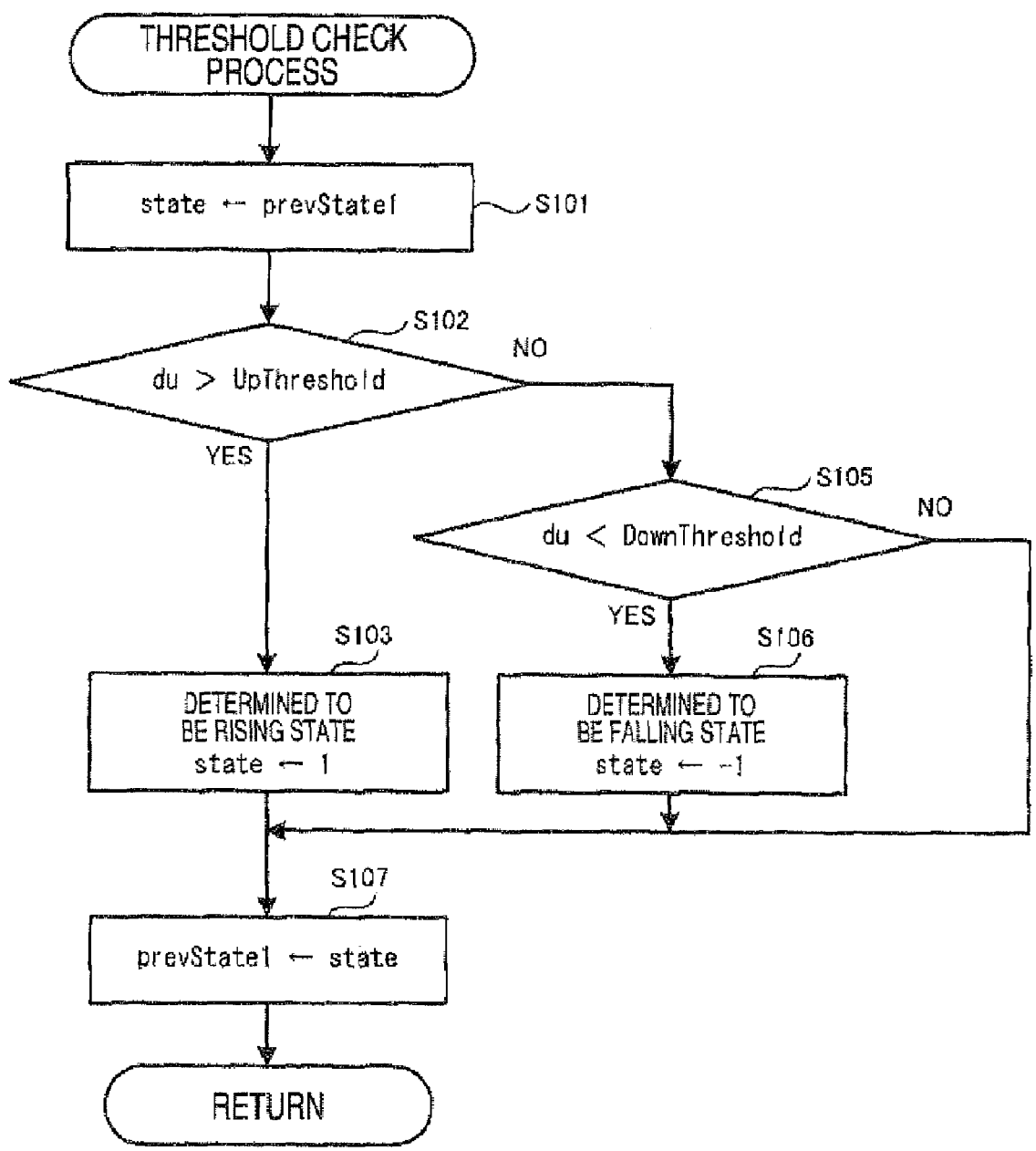
FIG. 10 is a flow chart of a threshold check process subroutine.
Figure 11:
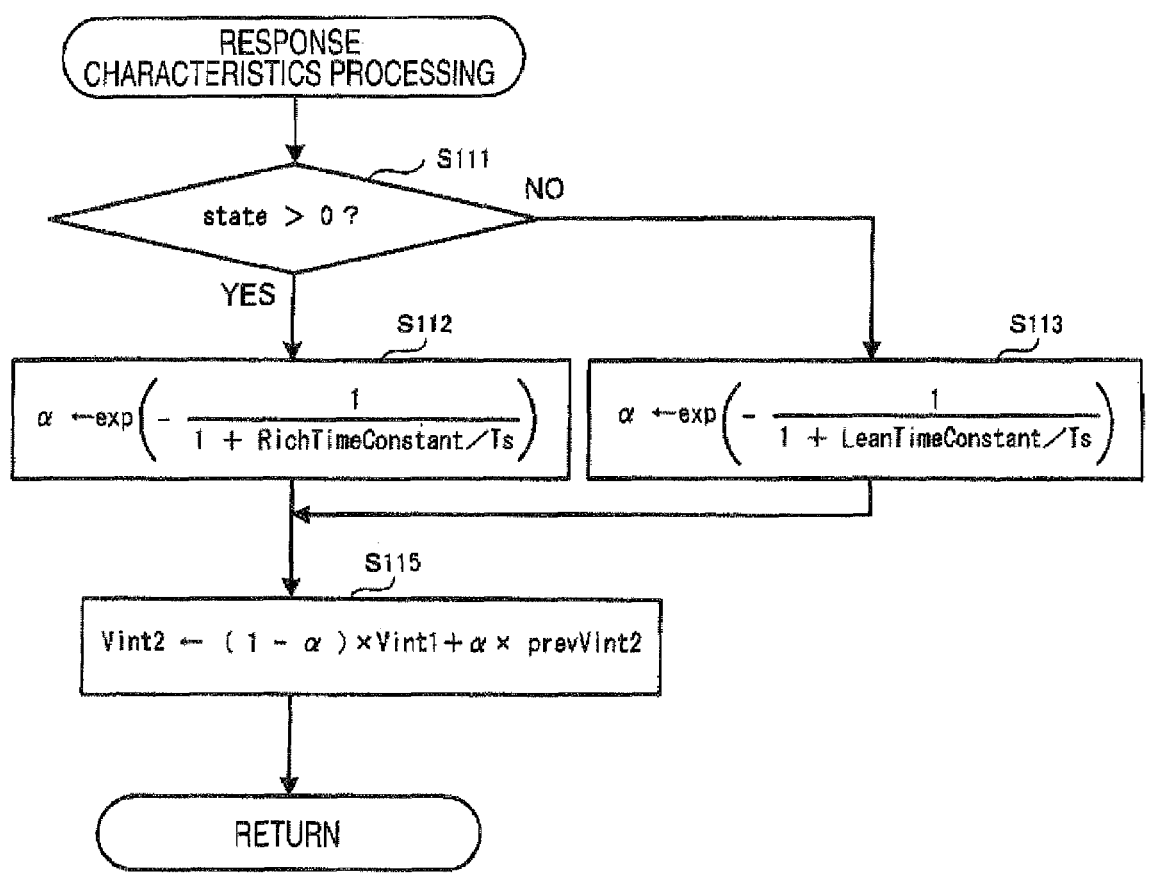
FIG. 11 is a flow chart of a response characteristics processing subroutine.
Figure 12:
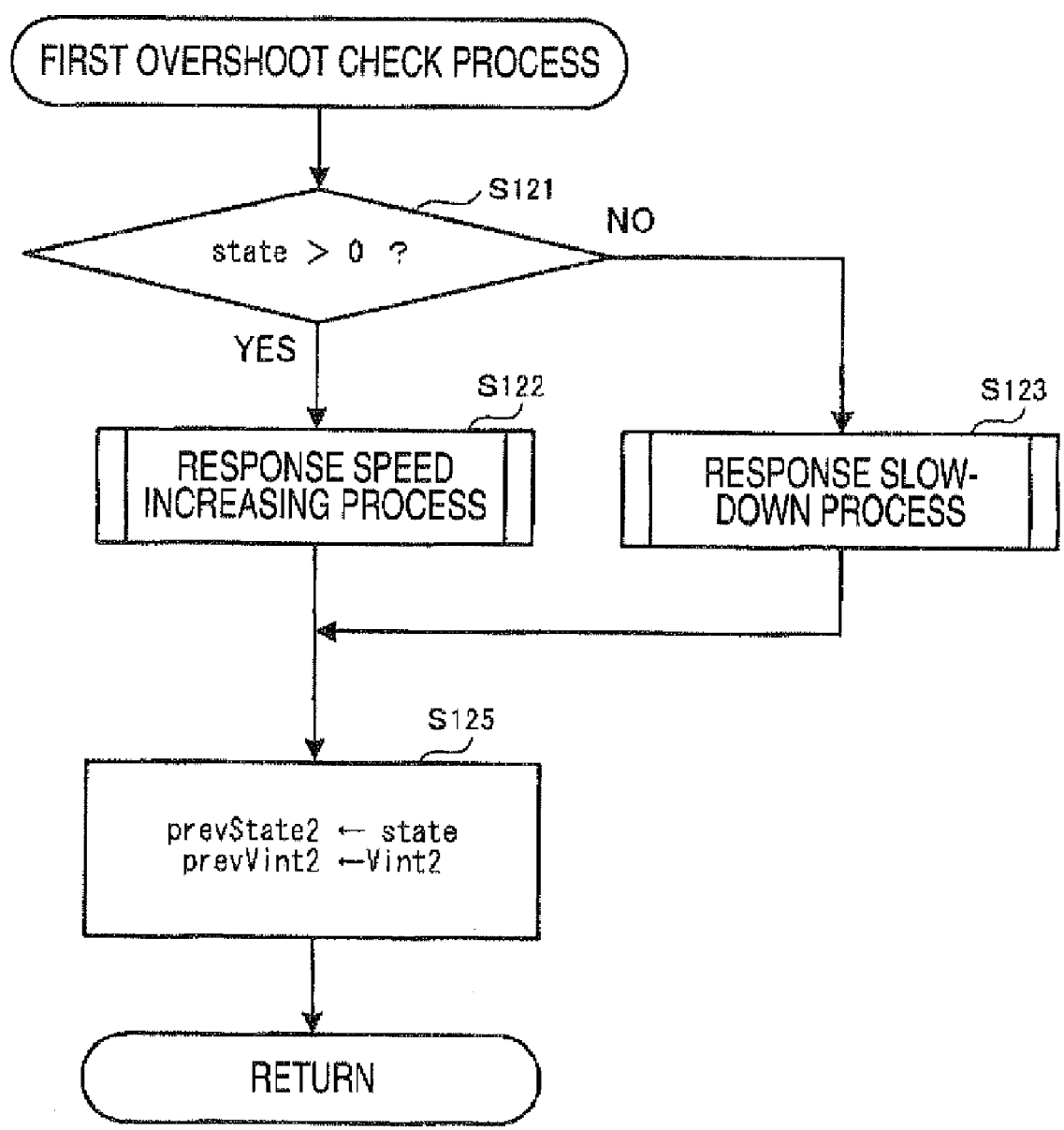
FIG. 12 is a flow chart of a first overshoot check process subroutine.
Figure 13:
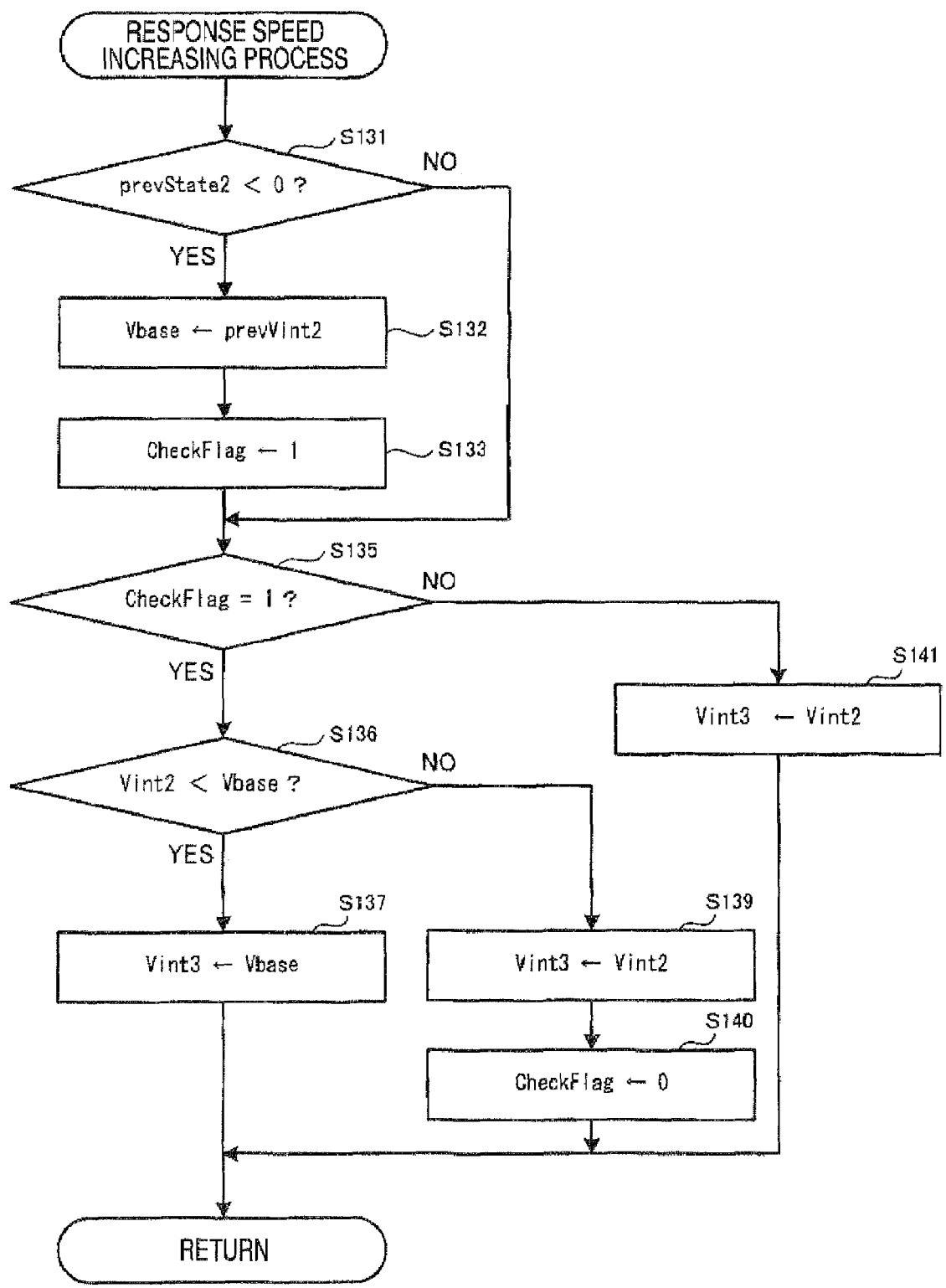
FIG. 13 is a flow chart of a response speed increasing process subroutine.
Figure 14:
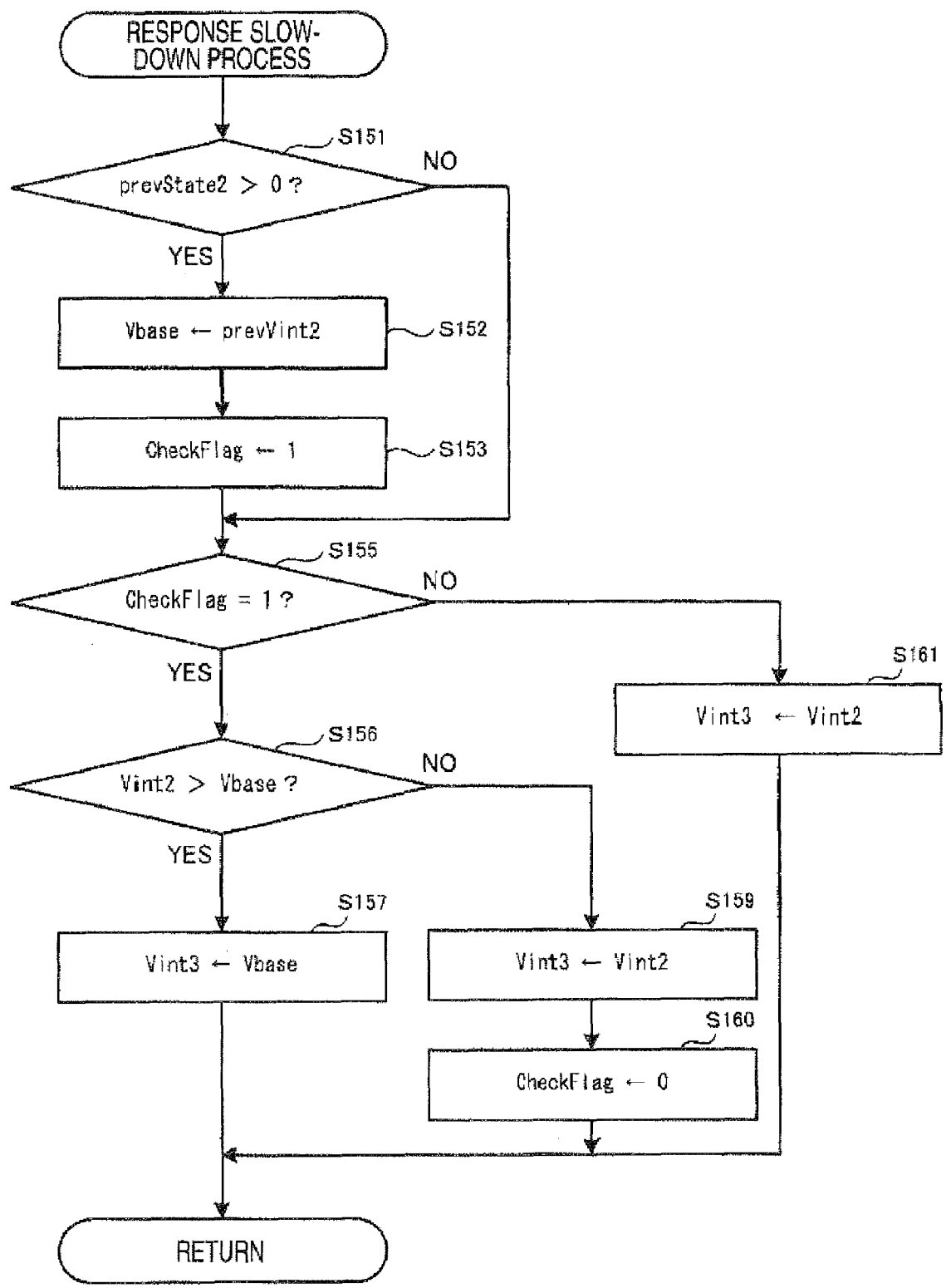
FIG. 14 is a flow chart of a response slow-down process subroutine.
Figure 15:
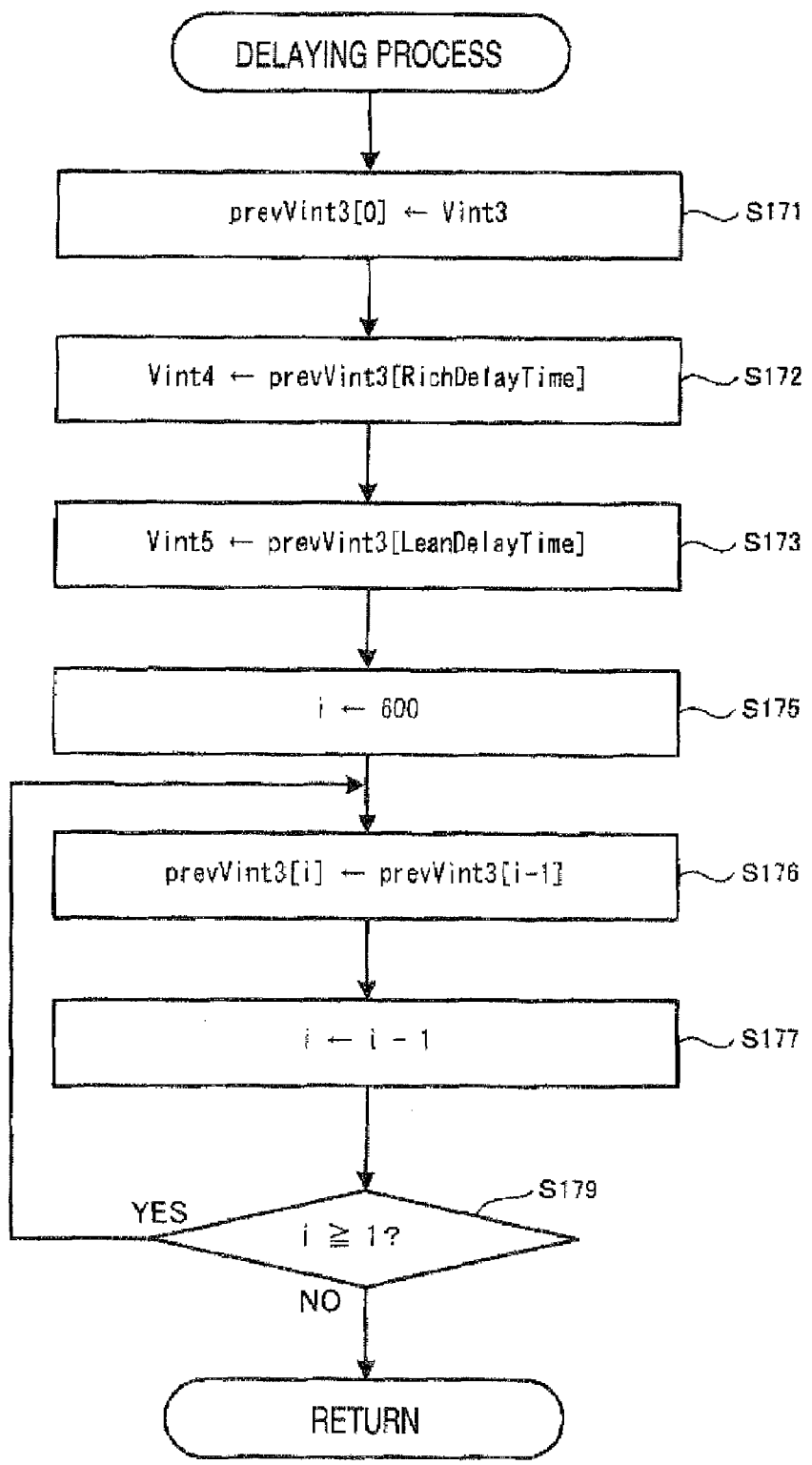
FIG. 15 is a flow chart of a delaying process subroutine.
Figure 16:
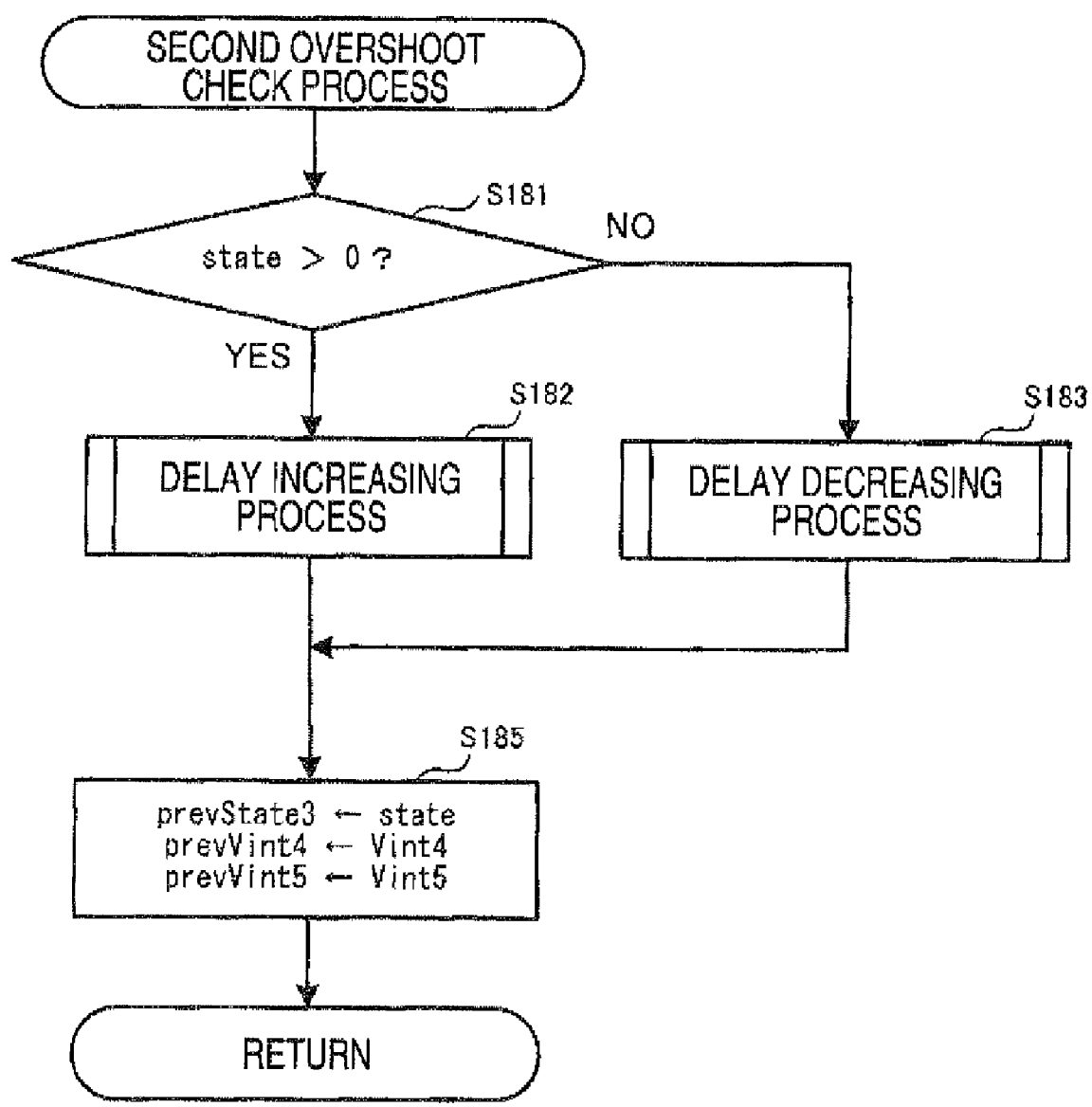
FIG. 16 is a flow chart of a second overshoot check process subroutine.
Figure 17:
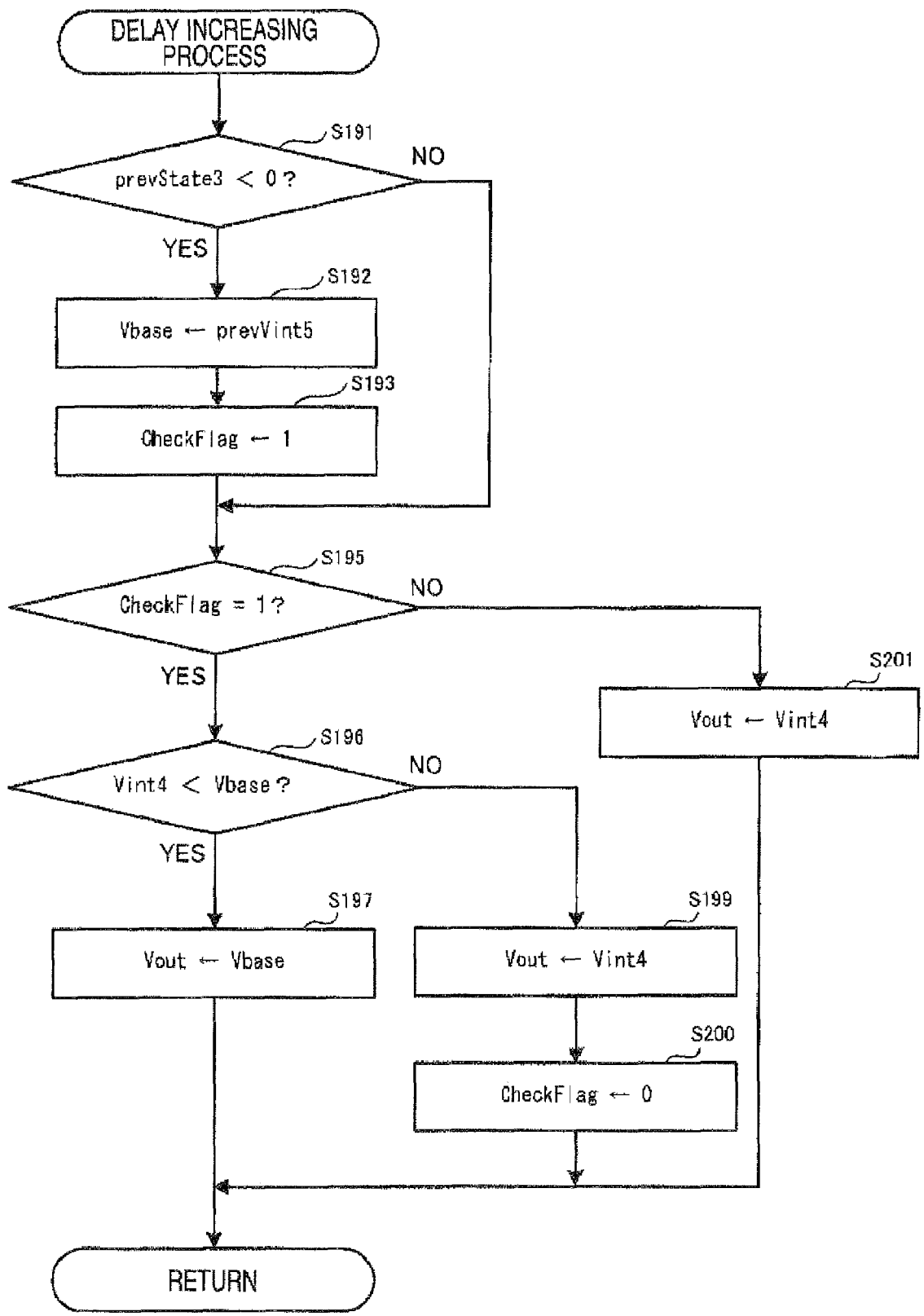
FIG. 17 is a flow chart of a delay increasing process subroutine.
Figure 18:
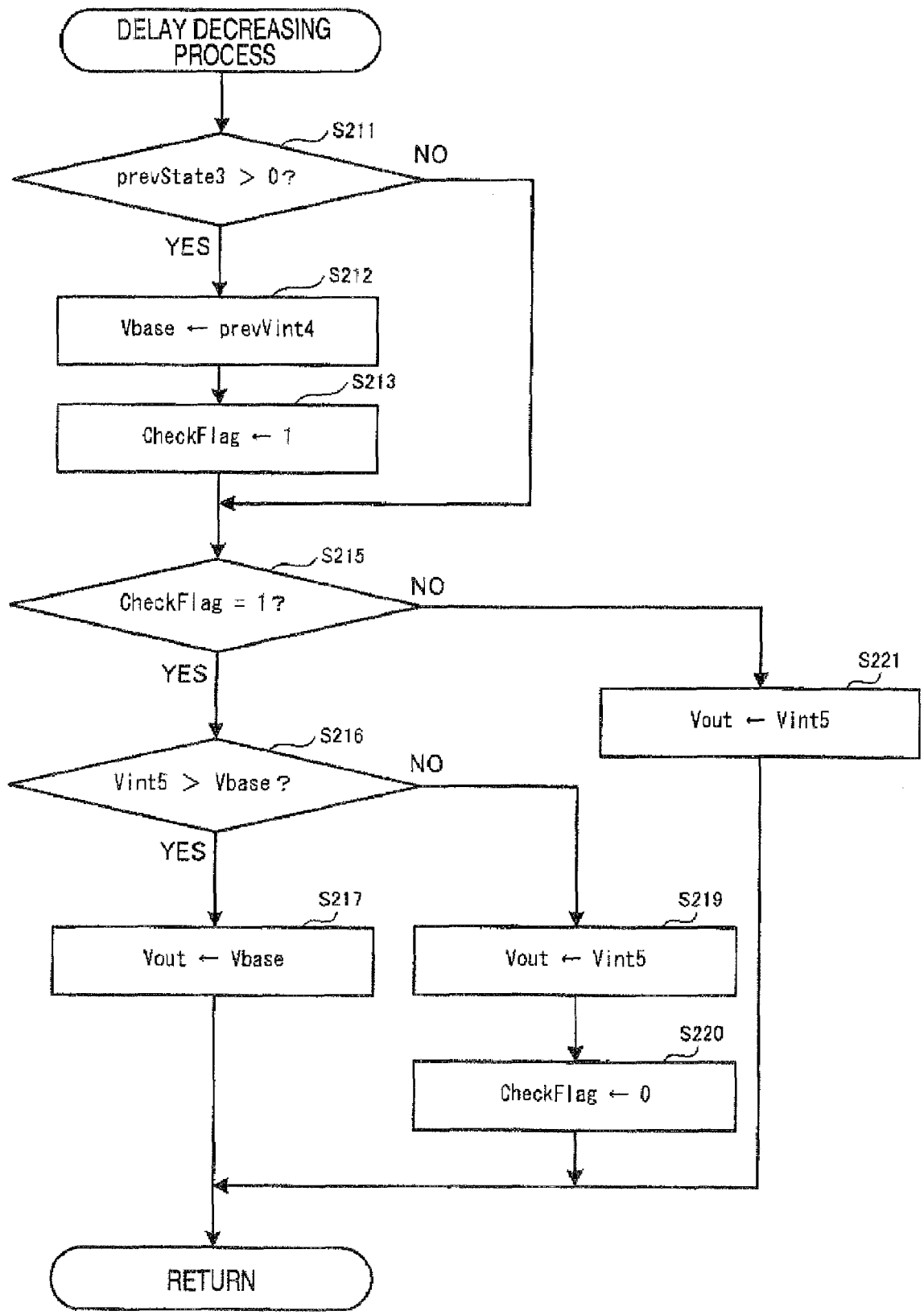
FIG. 18 is a flow chart of a delay decreasing process subroutine.

FIG. 5 is a flow chart showing a main routine of the deterioration signal generation program. FIG. 6 is a flow chart of a gain processing subroutine. FIG. 7 is a flow chart of a moving average process subroutine. FIG. 8 is a flow chart of a peak detection process subroutine. FIG. 9 is a flow chart of an average peak value calculation process subroutine. FIG. 10 is a flow chart of a threshold check process subroutine. FIG. 11 is a flow chart of a response characteristics processing subroutine. FIG. 12 is a flow chart of a first overshoot check process subroutine FIG. 13 is a flow chart of a response speed increasing process subroutine. FIG. 14 is a flow chart of a response slow-down process subroutine. FIG. 15 is a flow chart of a delaying process subroutine. FIG. 16 is a flow chart of a second overshoot check process subroutine. FIG. 17 is a flow chart of a delay increasing process subroutine. FIG. 18 is a flow chart of a delay decreasing process subroutine. Hereinafter, each step in the flow charts will be abbreviated as "S".

Figure 19:
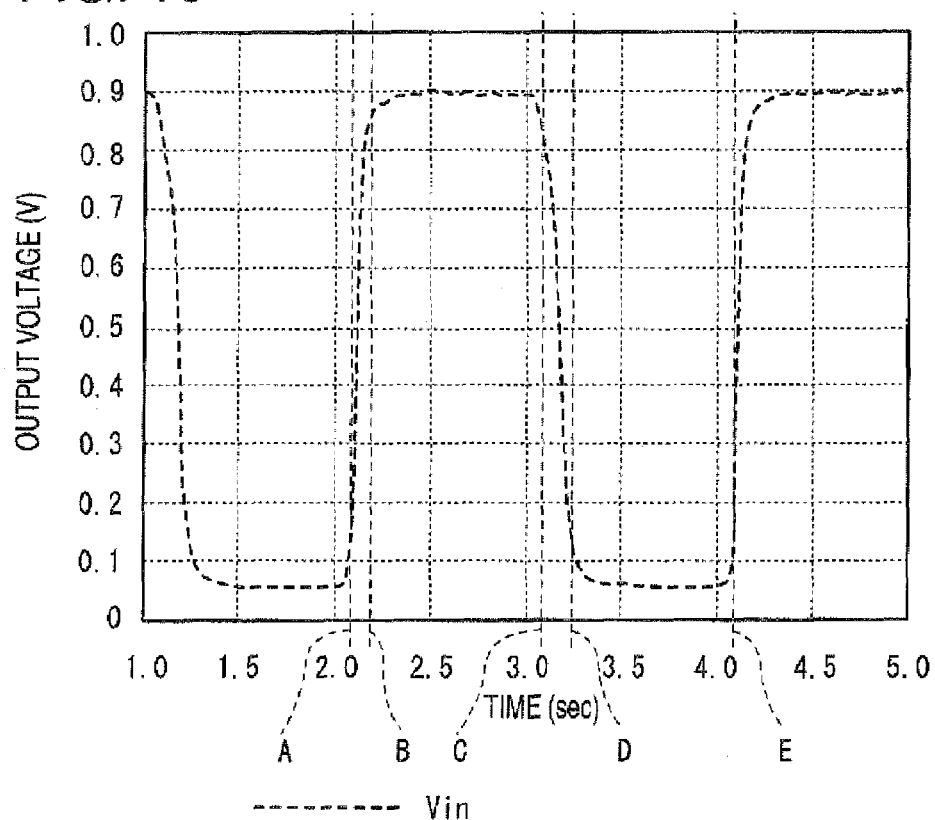
FIG. 19 is a graph showing an example of a reference signal obtained by alternating a target fuel-air ratio between rich and lean sides, the signal being plotted along a time axis.
Figure 20:
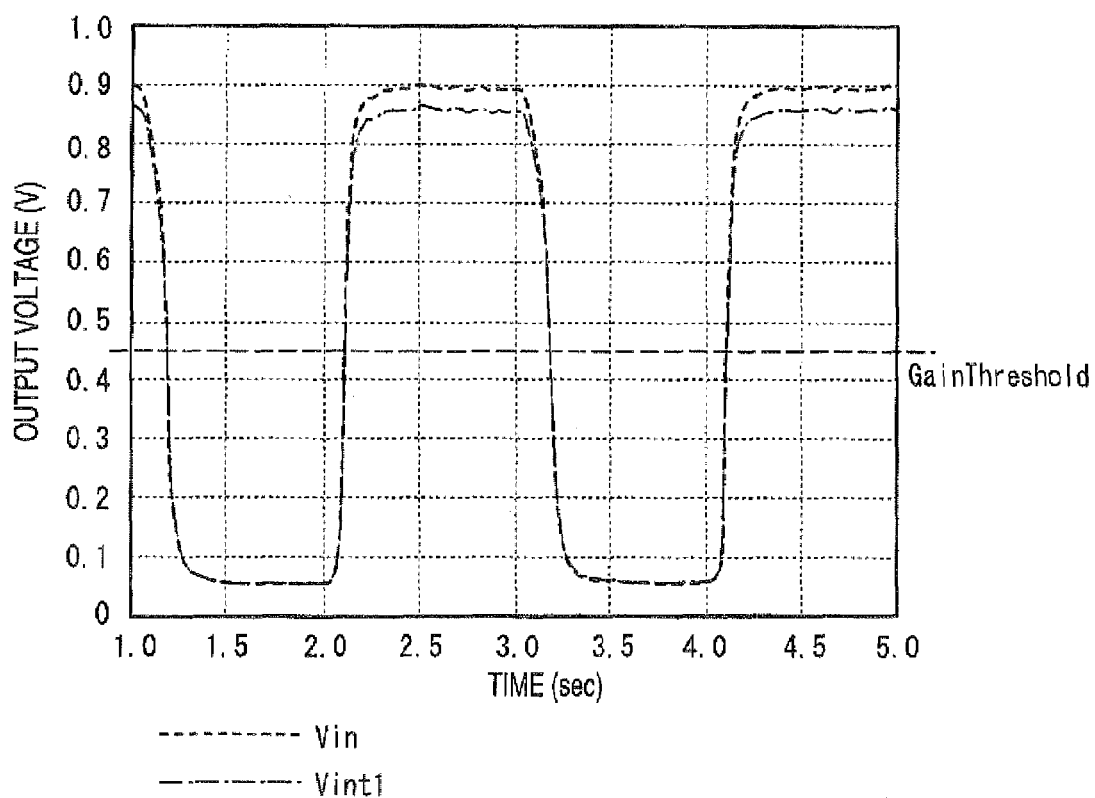
FIG. 20 is a graph showing an example of a deterioration signal obtained by changing a rich side gain of the reference signal shown in FIG. 19.
Figure 21:
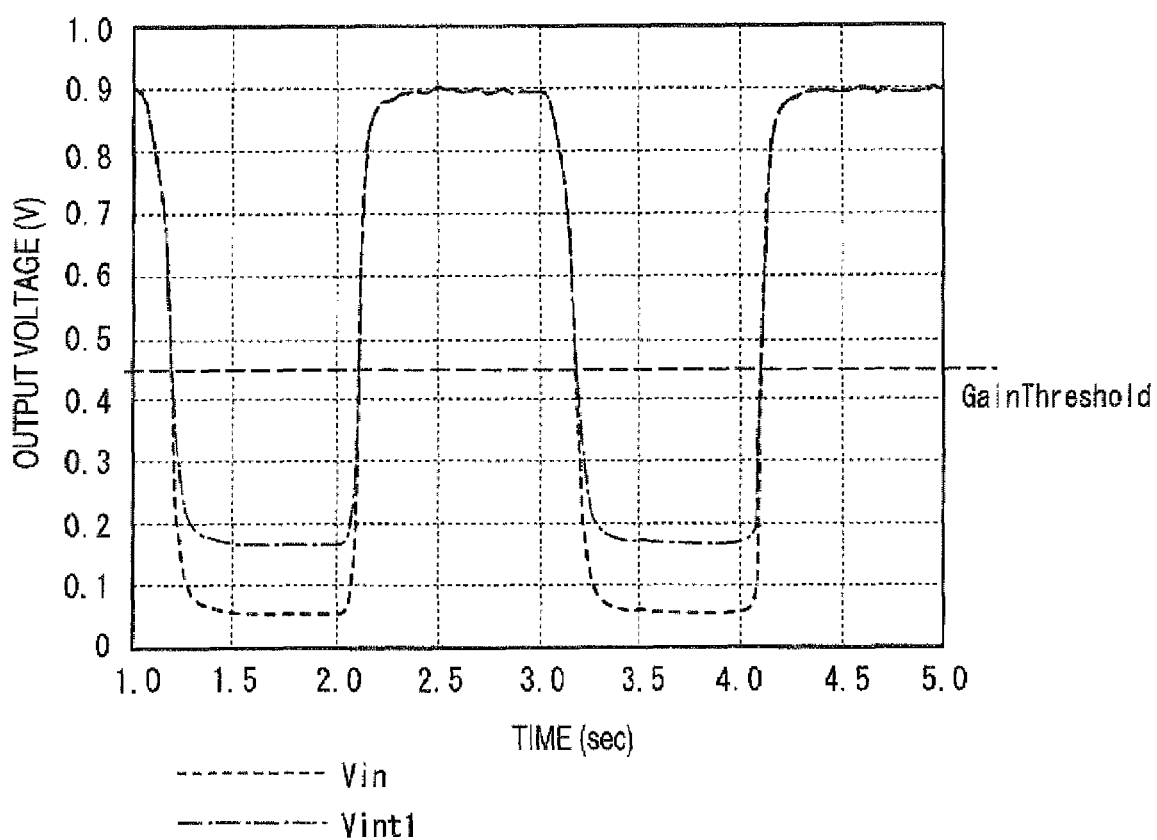
FIG. 21 is a graph showing an example of a deterioration signal obtained by changing a lean side gain of the reference signal shown in FIG. 19.
Figure 22:
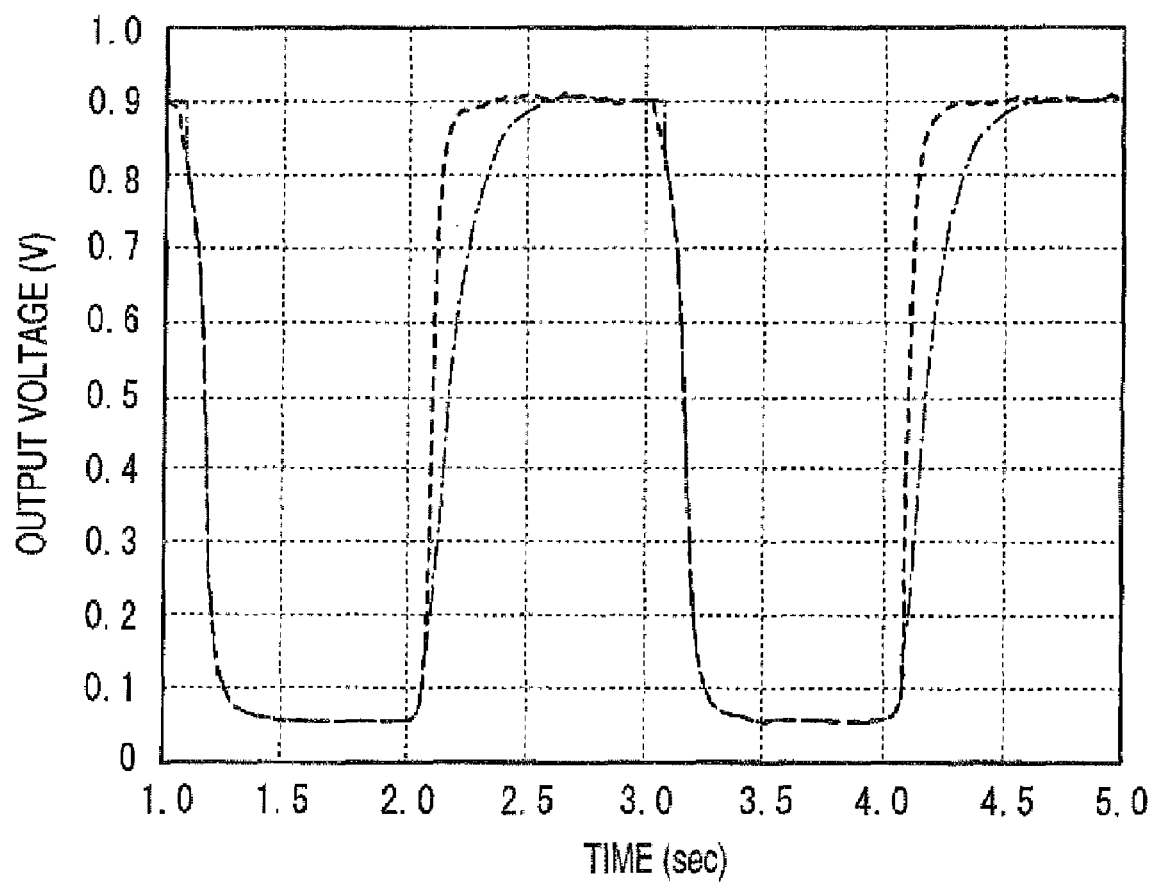
FIG. 22 is a graph showing an example of a deterioration signal obtained by changing rich side response characteristics of the reference signal shown in FIG. 19.
Figure 23:
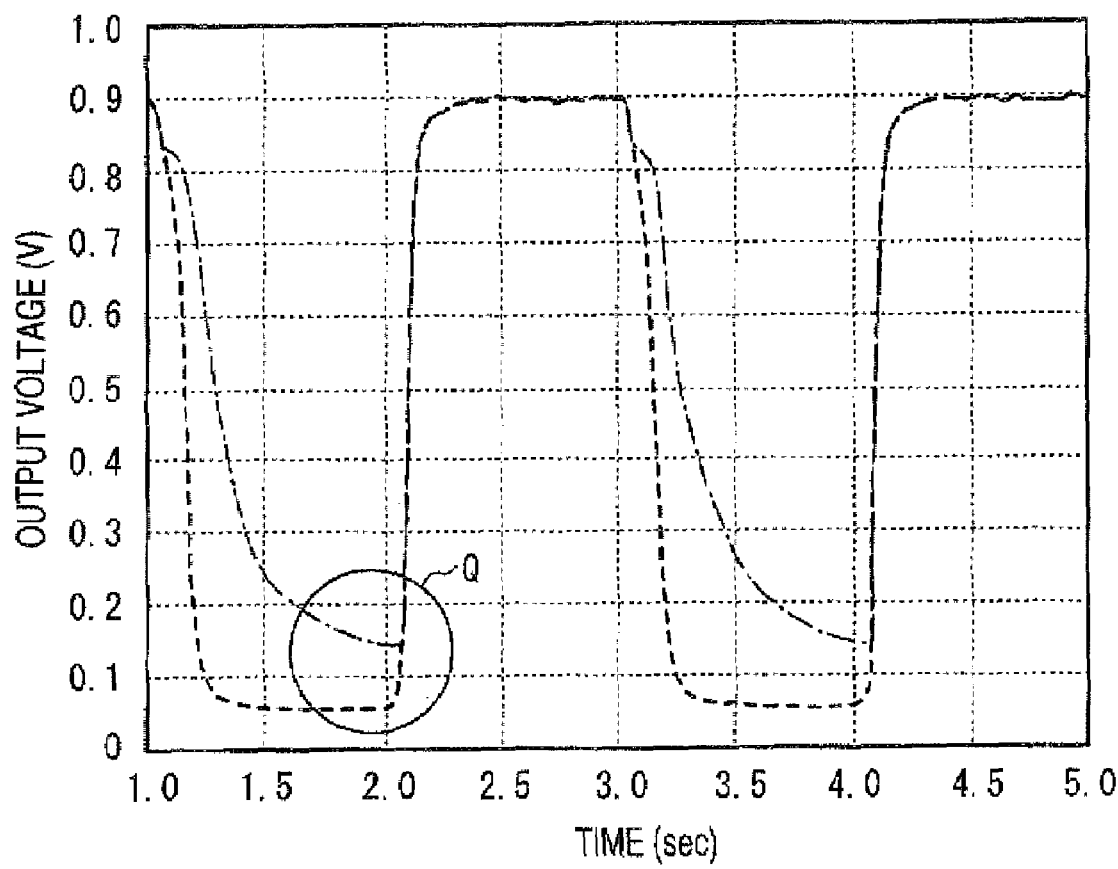
FIG. 23 is a graph showing an example of a deterioration signal obtained by changing lean side response characteristics of the reference signal shown in FIG. 19.
Figure 24:
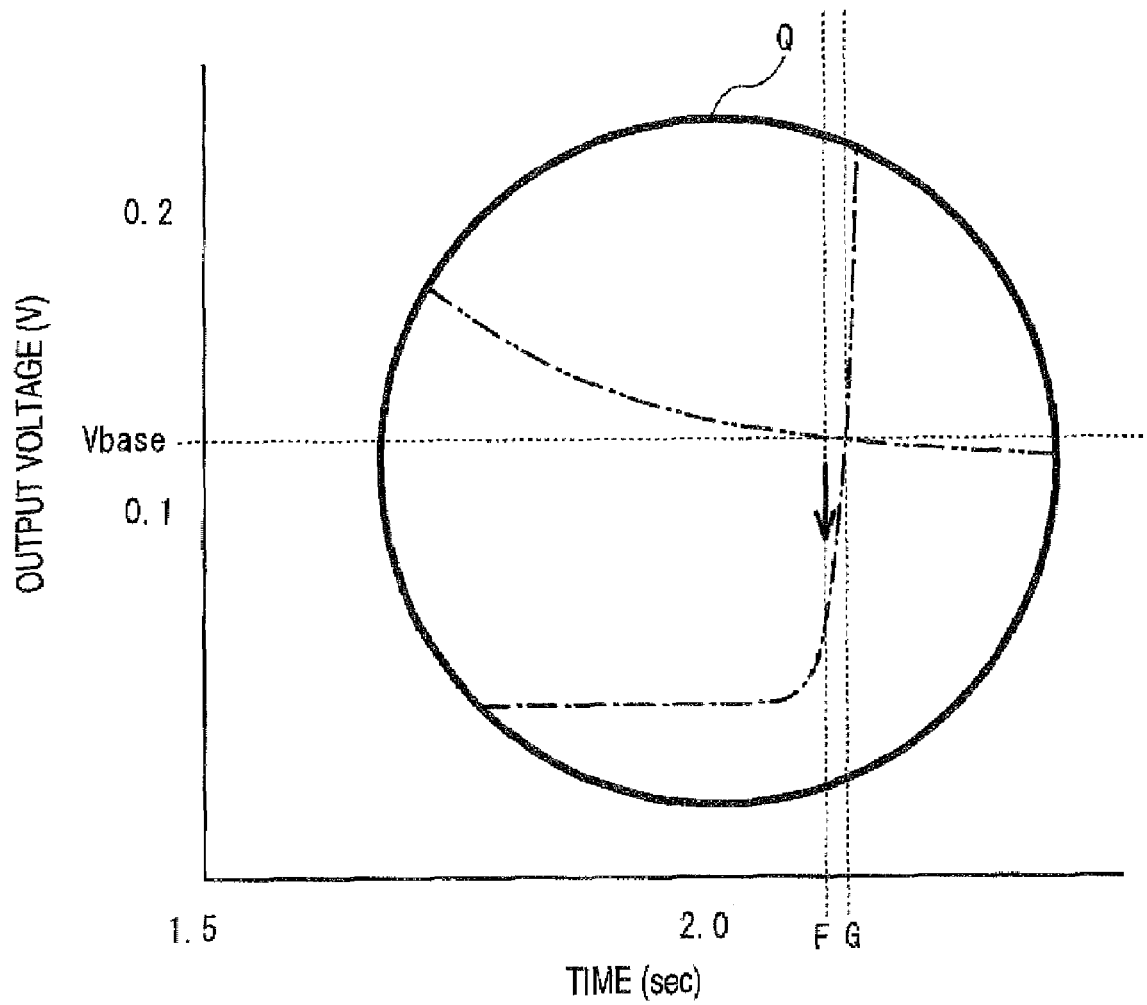
FIG. 24 is a graph showing the part of FIG. 23 indicated by a circle Q in an enlarged scale in order to explain a first overshoot check process.
Figure 25:
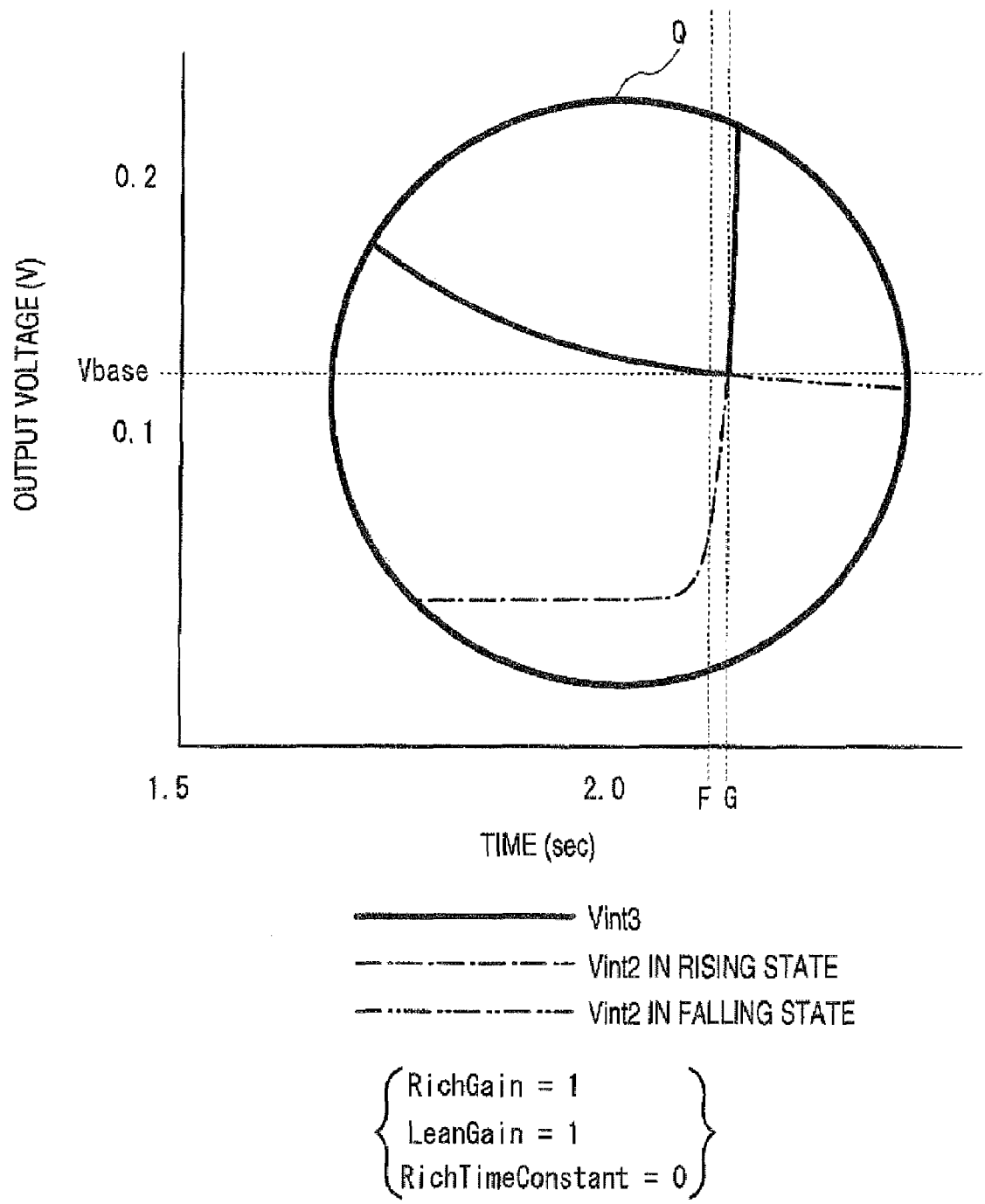
FIG. 25 is another graph showing the part of FIG. 23 indicated by the circle Q in an enlarged scale in order to explain the first overshoot check process.
Figure 26:
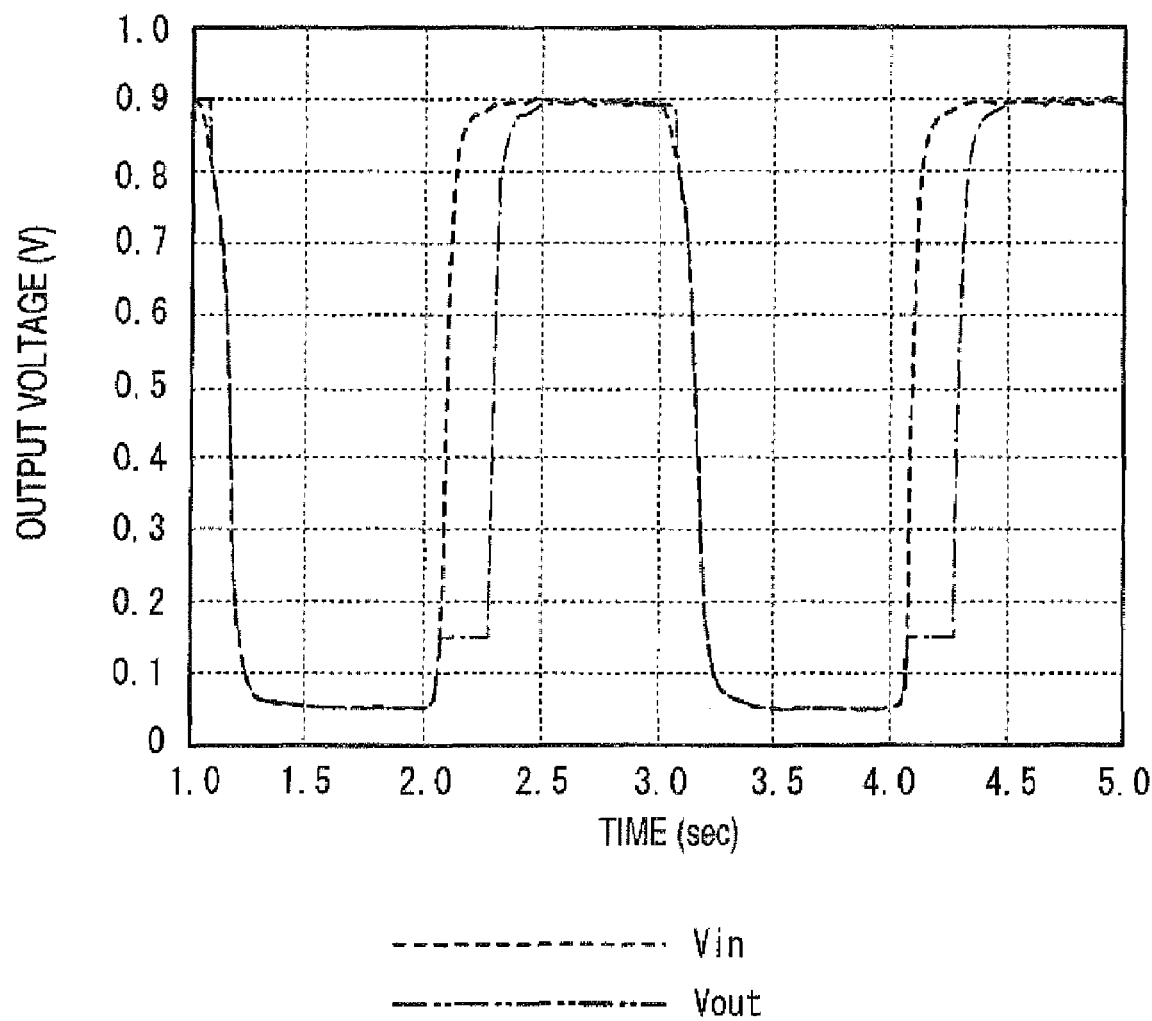
FIG. 26 is a graph showing an example of a deterioration signal obtained by changing a rich side delay time of the reference signal shown in FIG. 19.
Figure 27:
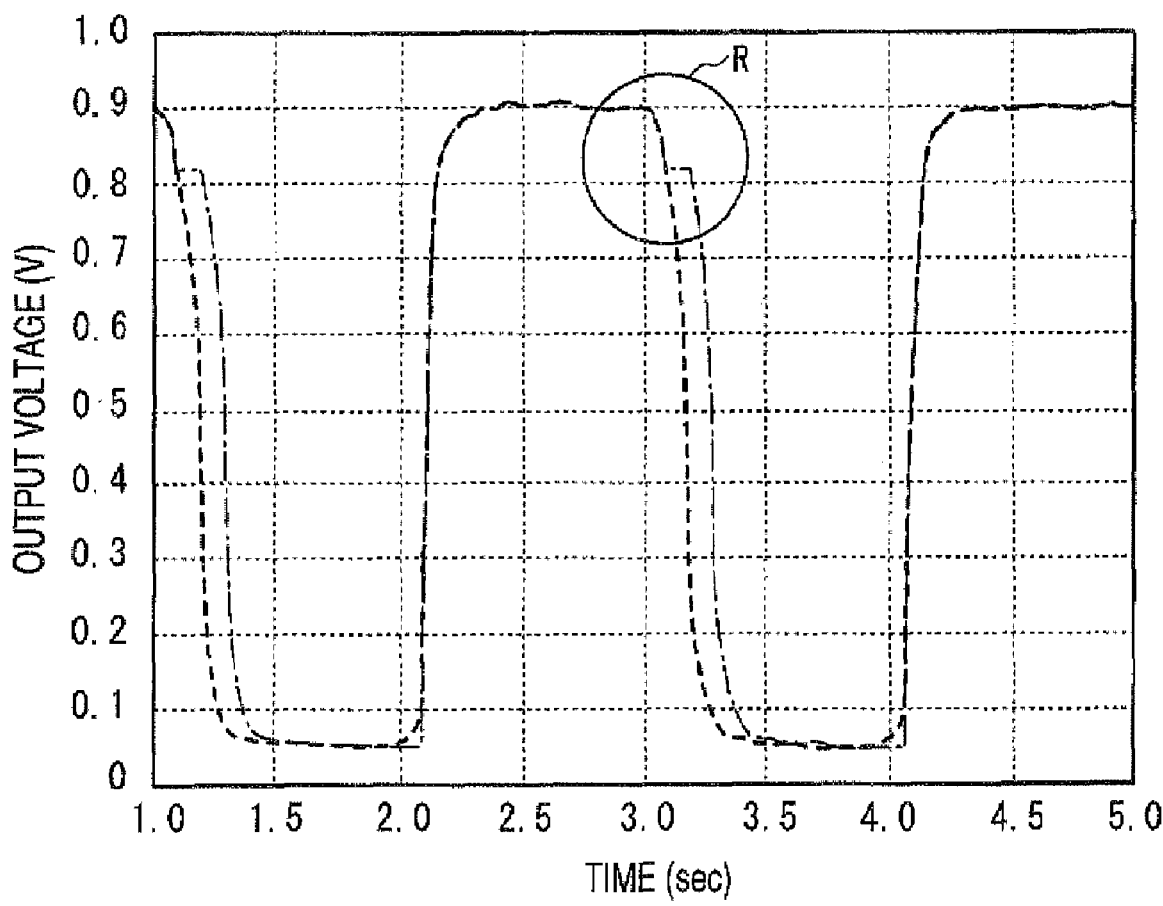
FIG. 27 is a graph showing an example of a deterioration signal obtained by changing a lean side delay time of the reference signal shown in FIG. 19.
Figure 28:
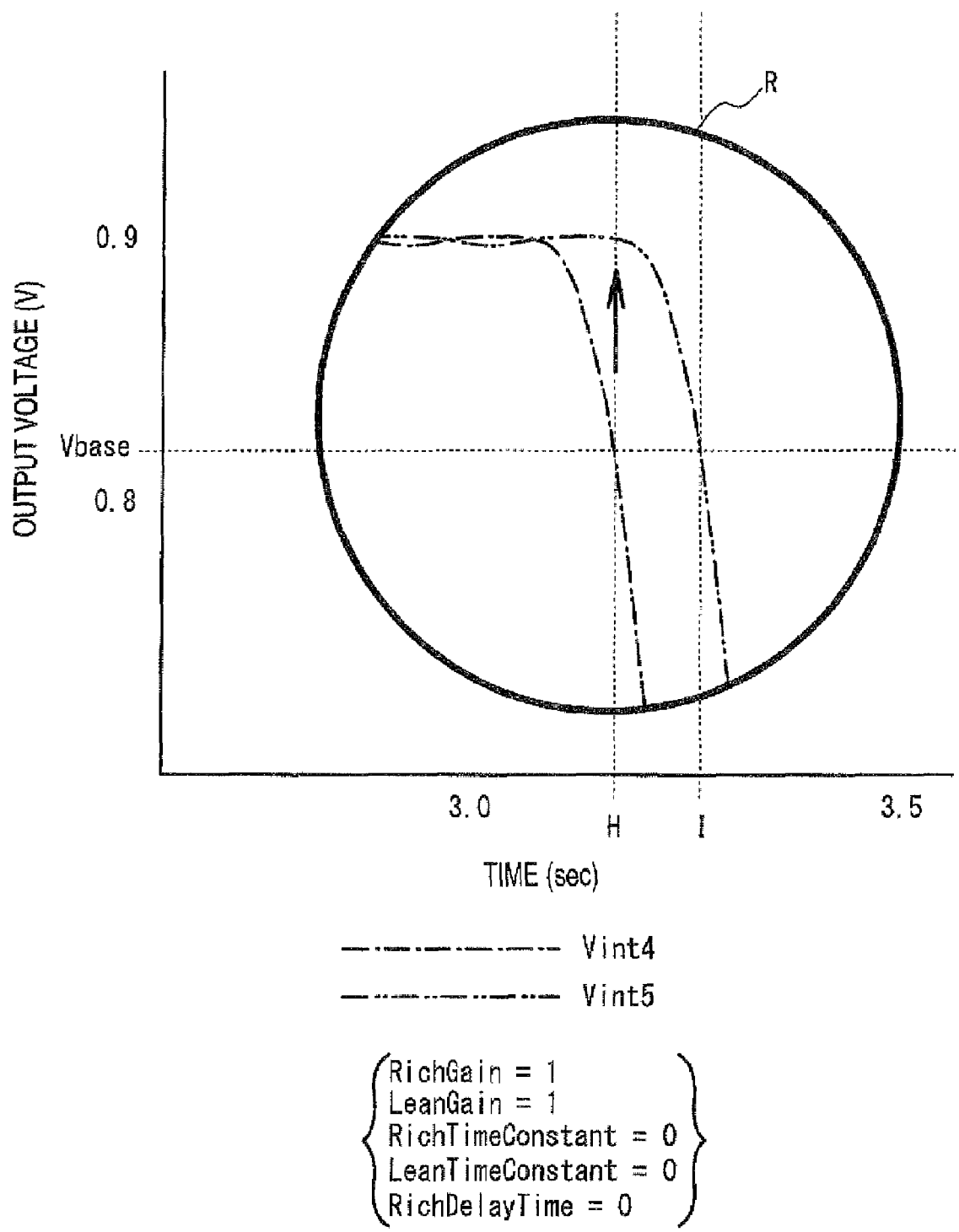
FIG. 28 is a graph showing the part of FIG. 27 indicated by a circle R in an enlarged scale in order to explain a second overshoot check process.
Figure 29:
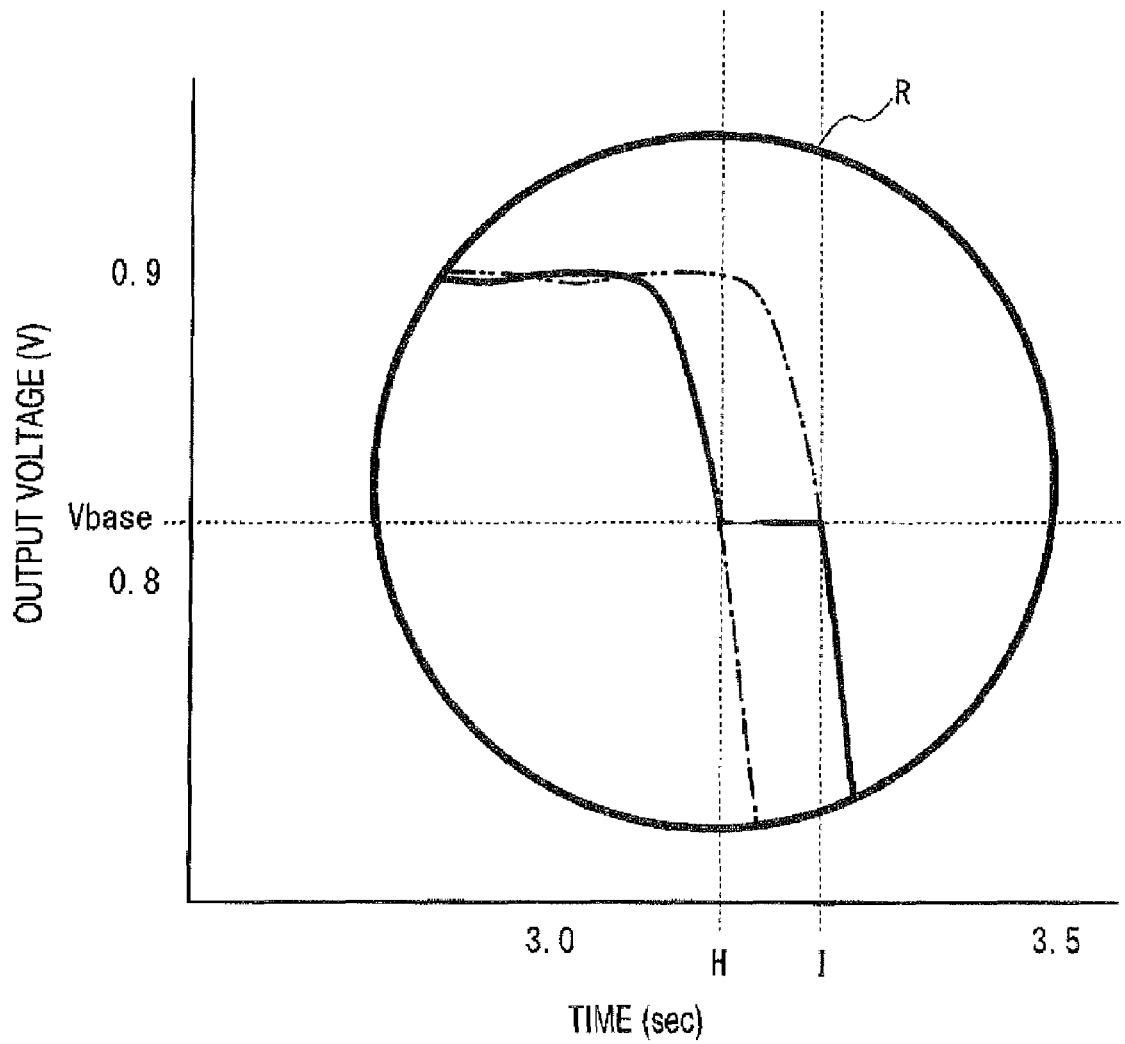
FIG. 29 is another graph showing the part of FIG. 27 indicated by the circle R in an enlarged scale in order to explain the second overshoot check process.
Figure 30:
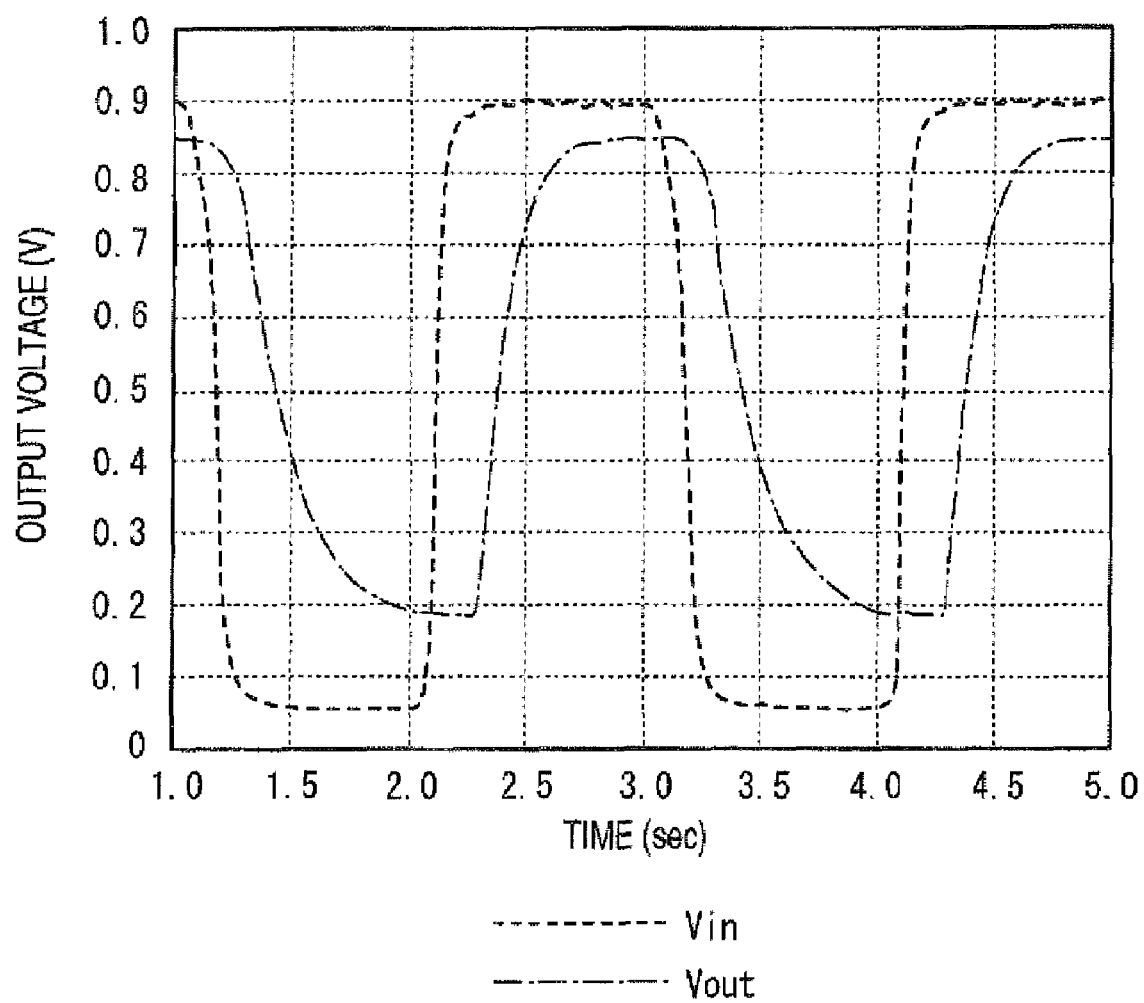
FIG. 30 is a graph showing an example of a deterioration signal obtained by changing the gain, response characteristics, and delay time of the reference signal shown in FIG. 19 on each of the rich side and lean side.

FIG. 19 is a graph showing an example of a reference signal obtained by alternating a target fuel-air ratio between the rich side and the lean side, the signal being plotted along a time axis. FIG. 20 is a graph showing an example of a deterioration signal obtained by changing a rich side gain of the reference signal show in FIG. 19. FIG. 21 is a graph showing an example of a deterioration signal obtained by changing a lean side gain of the reference signal shown in FIG. 19. FIG. 22 is a graph showing an example of a deterioration signal obtained by changing rich side response characteristics of the reference signal shown in FIG. 19. FIG. 23 is a graph showing an example of a deterioration signal obtained by changing lean side response characteristics of the reference signal shown in FIG. 19. FIG. 24 is a graph showing the part of FIG. 23 indicated by a circle Q in an enlarged scale in order to explain the first overshoot check process. FIG. 25 is another graph showing the part of FIG. 23 indicated by the circle Q in an enlarged scale in order to explain the first overshoot check process. FIG. 26 is a graph showing an example of a deterioration signal obtained by changing a rich side delay time of the reference signal shown in FIG. 19. FIG. 27 is a graph showing an example of a deterioration signal obtained by changing a lean side delay time of the reference signal shown in FIG. 19. FIG. 28 is a graph showing the part of FIG. 27 indicated by a circle R in an enlarged scale in order to explain the second overshoot check process. FIG. 29 is another graph showing the part of FIG. 27 indicated by the circle R in an enlarged scale in order to explain the second overshoot check process. FIG. 30 is a graph showing an example of a deterioration signal obtained by changing the gain, response characteristics, and delay time of the reference signal shown in FIG. 19 on each of the rich side and lean side.

Various types of set values are input by a user to the sensor simulator 1. Specifically, the set values include rich-side and lean-side gain factors (which are used as the values of the variables RichGain and LeanGain, respectively) and a gain threshold (which is used as the value of the variable GainThreshold) for changing the gain of the reference signal, rich-side and lean-side transition rates (which are used as the values of the variables RichTimeConstant and LeanTimeConstant, respectively) for changing the response characteristics of the reference signal, rich-side and lean-side delay times (which are used as the values of the variables RichDelayTime and LeanDelayTime respectively) for changing the starting point of a change in the reference signal. Those values are set by operating the input unit 60 and stored in the set value storage area 121 of the EEPROM 12, which allows set values which have been previously entered to be saved for later use even when the power supply of the sensor simulator is turned off.

The sensor simulator 1 starts generating a deterioration signal from the reference signal of the reference sensor 2 when the deterioration signal generation program shown in FIG. 5 is executed by being read from the program storage area 122 of the EEPROM 12 into the work area 131 of the RAM 13. According to the deterioration signal generation program shown in FIG. 5, an initialization process is first performed at step S1, and the process thereafter waits for a reset signal that is received every millisecond, at step S2. In the present embodiment, a timer program, which is not shown, is executed in parallel with the deterioration signal generation program, and a reset signal is output every millisecond. The process waits until a reset signal is received and proceeds to step S3 upon receipt of a reset signal. Then, subroutines of processes at steps S3 to S13 are sequentially called and executed to generate a deterioration signal based on the reference signal acquired from the reference sensor 2 and to output the signal to the ECU 3. After the process at Step S13, step S2 is entered again to wait for the reception of the next reset signal. That is, the processes at steps S3 to S13 for processing the reference signal into a deterioration signal is performed every millisecond. The specific contents of the processes of the deterioration signal generation program will be described below.

At the initialization process, various types of variables used by the deterioration signal generation program are initialized (S1). The initialization is carried out as follows. The above-described initial values stored in the initial value storage area 123 of the EEPROM 12 are read and stored in the respective storage areas in the variable storage area 132 of the RAM 13 as the values of the respective variables. The values of the seven variables (RichGain, LeanGain, GainThreshold, RichTimeConstant, LeanTimeConstant, RichDelayTime, and LeanDelayTime) set by a user in advance as described above are read from the set value storage area 121 of the EEPROM 12 and stored in the respective storage areas of the variable storage area 132 as the value of the respective variables. Referring to the processes at step S1 and subsequent steps of the deterioration signal generation program, the values of the variables are all read and written from and in the storage areas for the variables which are associated with the processes. Then, the process waits for the reception of a reset signal (S2: NO), and the subroutine of the gain process is called upon receipt of a reset signal (S2: YES, S3). At step S1, the CPU 11 reads delay times RichDelayTime and LeanDelayTime input by the user in advance through the input unit 60 and stored and saved in the EEPROM 12 to allow the deterioration signal generation program to use those variables and stores them in the variable storage area of the RAM 13. Therefore, the CPU 11 corresponds to the "delay time setting unit" according to the invention. At step S1, the CPU 11 similarly reads gain factors RichGain and LeanGain input by the user in advance through the input unit 60 and stored and saved in the EEPROM 12 to allow the deterioration signal generation program to use those variables and stores them in the variable storage area of the RAM 13. Therefore, the CPU 11 corresponds to the "gain factor setting unit" according to the invention. At step S1, the CPU 11 further reads transition rates RichTimeConstant and LeanTimeConstant input by the user in advance through the input unit 60 and stored and saved in the EEPROM 12 to allow the deterioration signal generation program to use those variables and stores them in the variable storage area of the RAM 13. Therefore, the CPU 11 corresponds to the "transition rate setting unit" according to the invention.

[Gain Processing]

Gain processing is a process of multiplying the voltage Vin of the reference signal by the different gain factors RichGain and LeanGain associated with fuel-air ratios of the exhaust gas residing on the rich side and lean side, respectively, to obtain the first intermediate signal (voltage Vint1). As mentioned above, the reference sensor 2 of the present embodiment is a λ-type oxygen sensor. It is known that a λ-type oxygen sensor, which is exposed to exhaust gas, has an output voltage of about 0.9 V when the fuel-air ratio of the exhaust gas is on the rich side and an output voltage of about 0.05 V when the ratio is on the lean side. When a target fuel-air ratio of a mixture is alternated between the rich side and lean side once per about 1 second, the voltage of the reference signal from the λ-type oxygen sensor or the reference sensor 2 undergoes an abrupt change between about 0.05 V and about 0.9 V once per about 1 second as shown in FIG. 19.

At the gain process shown in FIG. 6, the output voltage of the reference sensor 2 input through the A-D converter 30 is first acquired, and the voltage is stored as the variable Vin (S21). The voltage Vin of the reference signal thus acquired is compared with the threshold GainThreshold set by the user in advance (S22). Since the voltage of the reference signal varies between about 0.05 V and about 0.9 V as described above, the threshold GainThreshold is normally set at 0.45 V which is substantially in the middle of those voltages. When the voltage is greater than the threshold GainThreshold (S22: YES), it is determined that the voltage of the reference signal acquired is a voltage resulting from a fuel-air ratio on the rich side. Then, the surplus of the reference signal voltage over the threshold GainThreshold is multiplied by the gain factor RichGain to calculate a first intermediate signal (voltage Vint1) which has been changed only in the rich side gain thereof (S23). Specifically, "GainThreshold+(Vin− GainThreshold)×RichGain" is calculated, and the result is stored as Vint1. FIG. 20 shows an example in which the gain of the reference signal is changed only when the fuel-air ratio is on the rich side. In FIG. 20, the chain line represents a graph of a first intermediate signal (voltage Vint1) whose voltage is attenuated only when the reference signal has a voltage greater than 0.45 V as "GainThreshold" in comparison to a graph of the reference signal (voltage Vin) that is represented by the dotted line. When the voltage of the reference signal is 0.45 V or less, the graph of the first intermediate signal coincides with the graph of the reference signal. The CPU 11 which acquires the reference signal from the reference sensor 2 and stores the same as the voltage Vin at step S21 corresponds to the "reference signal acquisition unit" of the invention.

As shown in FIG. 6, when voltage Vin is lower than the threshold GainThreshold (S22: NO, S25: YES), it is similarly determined that the voltage of the reference signal acquire is a voltage resulting from a fuel-air ratio on the lean side. Then, the shortage of the reference signal voltage from the threshold GainThreshold is multiplied by the gain factor LeanGain to calculate a first intermediate signal (voltage Vint1) which has been changed only in the lean side gain thereof (S26). Specifically, "GainThreshold−(GainThreshold−Vin)×LeanGain" is calculated, and the result is stored as Vint1. FIG. 21 shows an example in which the gain of the reference signal is changed only when the fuel-air ratio is on the lean side. In FIG. 21, the chain line represents a graph of a first intermediate signal (voltage Vint1) whose voltage is amplified only when the reference signal has a voltage smaller than 0.45 V as "GainThreshold" in comparison to a graph of the reference signal (voltage Vin) that is represented by the dotted line. When the voltage of the reference signal is 0.45 V or more, the graph of the first intermediate signal coincides with the graph of the reference signal. The CPU 11 which changes the gain of the reference signal by the process at step S23 or S26 corresponds to the "gain changing unit" of the invention.

When the voltage Vin is equal to the threshold GainThreshold as shown in FIG. 6 (S22: NO, S25: NO), the process of changing the gain of the reference signal is not executed, and the voltage Vin is stored as the voltage Vint1 of the first intermediate signal (S27). When the voltage Vint1 of the first intermediate signal is obtained as thus described (S23, S26 or S27), the process proceeds to step S29. When the voltage Vint1 becomes out of a proper range of voltages, i.e., a range not lower than 0 V and lower than 5 V as a result of a gain change, a correction is made to keep the voltage in the proper range. Specifically, when the voltage Vint1 is 5 V or more (S29: YES), 4.99 V is stored as the voltage Vint1 (S30). On the other hand, when the voltage Vint1 is lower than 0 V (S29: NO, S31: YES), 0 V is stored as the voltage Vint1 (S33). When the voltage Vint1 is not lower than 0 V and lower than 5 V (S29: NO, S31: NO), it is determined that the voltage Vint1 is a proper value, and no correction is made, After the voltage Vint1 is thus corrected (S30/S33/S31: NO), the process returns to the main routine. The range of proper voltages of the first intermediate signal may be arbitrarily set.

[Moving Average Process]

Then, the main routine shown in FIG. 5 calls a subroutine for a moving average process (S5). The moving average process is a process of obtaining an average value du of differentials indicating changes in the reference signal in order to determine a change in the fuel-air ratio, i.e., a change from the rich side to the lean side or a change from the lean side to the rich side at a threshold check process (S7) which will be described later. In order to avoid erroneous determination at the threshold check process attributable to significant changes (fluctuations) of the reference signal in a short period, the average value du of differentials is calculated as an average value of 100 differentials, i.e., a differential Vdiff of the reference signal obtained by the execution of the latest moving average process plus differentials prevVdiff[1] to prevVdiff[99] of the reference signal obtained by the execution of 99 previous moving average processes.

As shown in FIG. 7, at the moving average process, a variable VdiffSum used in this subroutine is initialized, and 0 is stored as the variable (S41). Next, the difference between the voltage Vin of the reference signal acquired latest and the voltage prevVin of the reference signal acquired previously (1 ms ago) is calculated by "Vin−prevVin", and the difference is stored as the differential Vdiff of the reference signal acquired latest (S42). Since the reference signal is acquired every millisecond as described above, the differential Vdiff is obtained as an approximate value by the expression "Vin−prevVin". The differential Vdiff thus calculated is stored as the variable VdiffSum that is a sum value to obtain an average value of 100 differentials (S43).

At subsequent steps S45 to S49, processes of sequentially adding 99 previous differentials prevVdiff[1] to prevVdiff[99] of the reference signal to the sum VdiffSum are executed. First, 1 is stored as a variable i at step S45 (S45). Next, a value obtained by adding a differential prevVdiff[i(1)] calculated at an i-th previous differentiation (the immediately preceding differentiation in this case) to the sum VdiffSum is stored as a new sum value VdiffSum (S46). The value of the variable i is then incremented to 2 (S47), and the process thereafter returns to step S46 because i≦99 is satisfied (S49: YES). Then, a process of adding a differential prevVdiff[i(2)] to the sum VdiffSum is similarly executed. The series of processes is terminated when the value of the variable i exceeds 99 (S49: NO). After the processes are executed, the result of a calculation "Vdiff+prevVdiff[1]+prevdiff[2]+ . . . +prevVdiff[99]" is stored as the sum VdiffSum. Therefore, the sum of 100 differentials, e.g., the sum of differential of the reference signal acquired latest and 99 differentials of the reference signal acquired previously, is stored as the sum VdiffSum. At step S50, the sum is divided by 100 to calculate an average value, and the result is stored as the average differential du (S50).

At subsequent steps S51 to S57, processes are executed to update the differentials prevVdiff[i] which will then be used for calculating an average value of differentials when the next moving average process is executed. First, 99 is stored as the variable i at step S51 (S51). Next, a process of storing prevVdiff[i−1(98)] as a differential prevVdiff[i(99)] is executed (S53). The value of the variable i is then decremented to 98 (S54), and the process thereafter returns to step S53 because i≧2 is satisfied (S55: YES). Then, a process of storing prevVdiff[i−1(97)] as a differential prevVdiff[i(98)] is similarly executed. The series of processes is continued until the value of the variable i falls below 2 (S55: NO), and the values of the differentials prevVdiff[98] to prevVdiff[1] are stored to overwrite and update the values of the differentials prevVdiff[99] to prevVdiff[2], respectively. Finally, a differential Vdiff which has been calculated latest is stored to overwrite the differential prevVdiff[1], and the update is terminated (S57). Further, the voltage Vin of the reference signal is stored as a previous voltage prevVin of the reference signal to be used at step S42 when the next moving average process is executed (S58), the process then returns to the main routine.

[Peak Value Detection Process]

Next, the main routine shown in FIG. 5 calls a subroutine for a peak value detection process (S6). The peak value detection process is a process of obtaining thresholds UpThreshold and DownThreshold for the average value du of differentials representing changes in the reference signal, which are used at the threshold check process (S7) to be described later, the threshold UpThreshold allowing determination to be made on whether the fuel-air ratio has been changed from the lean side to the rich side or not, the threshold DownThreshold allowing determination to be made on whether the fuel-air ratio has been changed from the rich side to the lean side or not. Since changes in the average value du of differentials depend on the type of the sensor used, a maximum value (upward peak value) and a minimum value (downward peak value) of the average value du are identified every second. Therefore, the process is carried out to identify thresholds UpThreshold and DownThreshold suitable for the sensor by calculating them based on averages of upward and downward peak values in the last three seconds.

As shown in FIG. 8, the peak value detection process checks a count value StepCount used for measuring one second during which peak values are to be sampled. When the count value is less than 1000, it is determined that sampling of peak values is in progress (S61: YES). When an average value du of differentials obtained by the moving average process is greater than an upward peak value tmpUpPeak which is stored as a maximum value during the one second under sampling (S62: YES), the average value du is stored as tmpUpPeak to update the upward peak value (S63). When the average value du of differentials is equal to or smaller than the upward peak value tmpUpPeak (S62: NO) and smaller than a downward peak value tmpDownPeak which is stored as a minimum value during the one second under sampling (S65: YES), the average value du is similarly stored as tmpDownPeak to update the downward peak value (S66). When the average value du of differentials is not greater than the upward peak value tmpUpPeak (S62: NO) and not smaller than the downward peak value tmpDownPeak (S65: NO), peak values are not updated. After any of the above-described processes is executed (S63 or S66 or S65: NO), the count value StepCount is incremented (S67), and the process then returns to the main routine.

As described above, the processes at steps S3 to S13 of the main routine in FIG. 5 are executed every millisecond. Therefore, step S67 of the peak detection process in FIG. 8 is also executed every millisecond, and the count value StepCount continues to increase. After the initialization process at step S1 (see FIG. 5) or after the count value StepCount is reset at step S70 to be described later, the processes of the main routine are repeated every millisecond. When the count value StepCount reaches 1000 after the one second elapses (S61: NO), a subroutine for an average peak values calculation process is called (S69).

As shown in FIG. 9, at the average peak value calculation process, it is checked whether an upward peak value tmpUpPeak detected in the last one second is greater than one-third of an upward peak value prevUpPeak1 detected in the previous second (S91). When the value tmpUpPeak is a value equal to or smaller than one-third of prevUpPeak1 (S91: NO), it is determined that the upward peak value tmpUpPeak detected in the last one second has been a noise. Then, a value that is 0.9 times the upward peak value prevUpPeak1 detected in the previous second is stored as tmpUpPeak (S92), and the process proceeds to step S93. When the value tmpUpPeak is a value greater than one-third of prevUpPeak1 (S91: YES), the process proceeds to step S93 directly. At step S93, an average value of three upward peak values detected latest is calculated. Specifically, "(tmpUpPeak+prevUpPeak1+prevUpPeak2)/3" is calculated, and the result of the calculation is stored as an average upward peak value UpPeak (S93).

A similar process is executed on downward peak values. Specifically, when a downward peak value tmpDownPeak detected in the last one second is equal to or greater than one-third of a downward peak value prevDownPeak1 detected in the previous second (S95: NO), it is determined that the downward peak value tmpDownPeak detected in the last one second has been a noise. Then, a value that is 0.9 times the downward peak value prevDownPeak1 detected in the previous second is stored as tmpDownPeak (S96), and the process proceeds to step S97. When the value tmpDownPeak is a value smaller than one-third of prevDownPeak1 (S95: YES), the process proceeds to step S97 directly. At step S97, an average value of three downward peak values detected latest is similarly calculated. Specifically, "(tmpDownPeak+prevDownPeak1+prevDownPeak2)/3" is calculated, and the result of the calculation is stored as an average downward peak value DownPeak (S97).

Then, each variable is updated for the use of the same in calculating an average upward peak value and an average downward peak value when the next average peak value calculation process is executed one second later. Specifically, the upward and downward peak values prevUpPeak1 and prevDownPeak1 detected in the previous second are stored to overwrite an upward peak value and a downward peak value prevUpPeak2 and prevDownPeak2 detected in the second before the previous second. The upward and downward peak values tmpUpPeak and tmpDownPeak detected in the last one second are stored to overwrite the upward and downward peak values prevUpPeak1 and prevDownPeak1 detected in the previous second. Further, 0 is stored as tmpUpPeak and tmpDownPeak to reset the upward peak value and the downward peak value (S99).

Thereafter, when the process returns to the peak value detection process subroutine shown in FIG. 8, 0 is stored as the count value StepCount to reset the time measurement for detecting an upward peak value and a downward peak value in the next one second (S70). At subsequent steps S71 to S81, a correction is made to keep the average upward and downward peak values UpPeak and DownPeak obtained at the average peak value calculation process in respective ranges of proper values. Specifically, the average upward peak value UpPeak is determined to be proper when it is not smaller than 0 and not greater than 0.0067 (S71: NO, S74: NO). When the peak value UpPeak is smaller than 0 (S71: YES), 0.005 is stored as the peak value UpPeak (S73). When the peak value UpPeak is greater than 0.0067 (S71: NO, S74: YES), 0.0067 is stored as the peak value UpPeak (S75).

After the peak value UpPeak is corrected (S73, S75, S74: NO), the process proceeds to step S77 to execute a similar correction on the peak value DownPeak. Specifically, the average downward peak value DownPeak is determined to be proper when it is not smaller than −0.0067 and not greater than 0 (S77: NO, S79: NO). When the peak value DownPeak is greater than 0 (S77: YES), −0.005 is stored as the peak value DownPeak (S78). When the peak value DownPeak is smaller than −0.0067 (S77: NO, S79: YES), −0.0067 is stored as the peak value DownPeak (S81). After the peak value DownPeak is also corrected as thus described (S78, S81, S79: NO), the process proceeds to step S82.

At step S82, a process of obtaining thresholds UpThreshold and DownThreshold to be used at a subsequent threshold check process (S7) is executed (S82). In the present embodiment, a value that is 0.15 times the average upward peak value UpPeak is set as the threshold Upthreshold, and a value that is 0.15 times the average downward peak value DownPeak is set as the threshold DownThreshold. The process thereafter returns to the main routine. Values calculated when the process at step S82 is executed latest are stored as the thresholds UpThreshold and DownThreshold obtained as described above until the count value StepCount is smaller than 1000, and those values will be used at a subsequent threshold check process.

[Threshold Check Process]

Next, the main routine shown in FIG. 5 calls a subroutine for a threshold check process (S7). The threshold check process is a process of comparing an average value du of differentials of the reference signal obtained at the moving average process with thresholds UpThreshold and DownThreshold obtained at the peak value detection process to determine whether the average value is increasing or decreasing.

As shown in FIG. 10, the threshold check process is a process of copying and storing the value prevState1 in the "state" flag to use the value in the current process (S101), prevState1 being the value of the "state" flag indicating the result of the detection of changes in the fuel-air ratio determined at the threshold check process executed previously (1 ms ago). Next, the average value du and the upward threshold UpThreshold are compared. When the average value du exceeds to the upward threshold UpThreshold (S102: YES), it is determined that the voltage of the reference signal has abruptly increased and the fuel-air ratio has been changed from the Lean side to the rich side or in a rising state, and 1 is stored in the "state" flag (S103). Similarly, when the average value du is smaller than the downward threshold DownThreshold, it is determined that the voltage of the reference signal has abruptly decreased and that the fuel-air ratio has been changed from the rich side to the lean side or in a falling state, and −1 is stored in the "state" flag (S106). When the average value du is not smaller than the downward threshold DownThreshold and not greater than the upward threshold UpThreshold (S102: NO, S105: NO), no change is made to the previously determined flag value. After the state of the fuel-air ratio is determined as thus described (S103/S106/S105: NO), the current value of the "state" flag is stored as prevState1 to use the value at the next threshold check process (S107), and the process then returns to the main routine. The point in time when the average value du is determined to be in the excess of the upward threshold UpThreshold or in a rising state and 1 is newly set as the value of the "state" flag at step S102 is the "lean-rich change starting point" according to the invention. The point in time when the average value du is determined to be smaller than the downward threshold DownThreshold or in a falling state and −1 is newly set as the value of the "state" flag at step S103 is the "rich-lean change starting point" according to the invention. The CPU 11 which executes the determination processes at steps S102 and S103 corresponds to the "fuel-air ratio change starting point detection unit" according to the invention.

Specific examples of operations at the threshold check process will now be described with reference to the graph in FIG. 19. When a target fuel-air ratio is changed from the lean side to the rich side, the voltage (output voltage) of the reference signal abruptly increases as seen in the section A-B. Specifically, the average value du of differentials of the reference signal is great enough to satisfy the relationship du>UpThreshold and is therefore determined to be rising in this section, and 1 is stored in the "state" flag. In the section B-C where the voltage of the reference signal reaches about 0.9 V and becomes stable, the average value du of differentials of the reference signal does not fall below the downward threshold DownThreshold, although it approaches 0. In this section, since the previous value of the "state" flag which has been copied from the "prevState1" flag is maintained as it is, the "state" flag is 1, and the increasing state is maintained. When the target fuel-air ratio is changed from the rich side to the lean side, the voltage of the reference signal abruptly decreases as shown in the section C-D. The average value du of differentials of the reference signal is a great negative value satisfying the relationship du<DownTheshold, and the average value is determined to be falling in this section. Therefore, −1 is stored in the "state" flag. In the section D-E where the voltage of the reference signal reaches about 0.05 V and becomes stable, the average value du of differentials of the reference signal does not fall below the downward threshold DownThreshold, although it approaches 0. In this section, since the previous value of the "state" flag which has been copied from the "prevState1" flag is maintained as it is, the "state" flag is −1, and the decreasing state is maintained. The state of the fuel-air ratio determined as thus described is used in response characteristics processing at step S9, a first overshoot check process at step S10, and a second overshoot check process at step S13.

[Response Characteristics Processing]

Next, the main routine shown in FIG. 5 calls a subroutine for response characteristics process (S9). The response characteristics processing is a process of obtaining a second intermediate signal (voltage Vint2) by changing response characteristics of the reference signal (voltage Vin) (or the first intermediate signal (voltage Vint1 obtained through gain processing in the present embodiment)) using a transition rate RichTimeConstant or LeanTimeConstant depending on the sate of the fuel-air ratio, i.e., the increasing state or decreasing state.

In the response characteristics processing shown in FIG. 11, reference is made to the value of the "state" flag obtained at the threshold check process to check whether the value is greater than 0 or not (S111). In the increasing state, the "state" flag is 1 (S111: YES), the lean-rich transition rate RichTimeConstant is selected. A coefficient α is calculated using Expression 2 shown above, and the result of the calculation is stored (S112). In the decreasing state in which the "state" flag is −1 (S111: NO), the rich-lean transition rate LeanTimeConstant is similarly selected. The coefficient α is calculated using Expression 3 shown above, and the result of the calculation is stored (S113).

Then, Expression 1 shown above is used to calculate a voltage Vint2 of a second intermediate signal which is obtained by changing response characteristics of the voltage Vint1 of the first intermediate signal (S115). At this time, the coefficient α calculated by executing the process at step S112 or S113 and prevVint2 that is the voltage Vint2 stored at the previous response characteristics processing are used as variables in Expression 1. The process thereafter returns to the main routine. The CPU 11 which changes the response characteristics of the reference signal (the first intermediate signal in the present embodiment) at the process of step S115 using the coefficient α calculated at the process of the step S112 or S113 corresponds to the "transition time changing unit" of the invention.

[First Overshoot Check Process]

When the fuel-air ratio is changed, the transition rate (RichTimeConstant or LeanTimeConstant) which has been used for the calculation of the second intermediate signal is switched to the other transition rate (LeanTimeConstant or RichTimeConstant). The switching of the transition rate takes place at timing when a change in the reference signal as a result of a change in the fuel-air ratio is detected, and the voltage Vin of the reference signal (the voltage Vint1 of the first intermediate signal in the present embodiment) may have already started changing (increasing or attenuating) significantly at that timing. For this reason, the direction of the change in the calculated voltage Vint2 of the second intermediate signal may be temporarily reversed at that timing. For example, when the fuel-air ratio is changed from the lean side to the rich side, the voltage Vint2 of the second intermediate signal changes from low potential to high potential. However, a change from high potential to low potential may temporarily take place at the timing described above, and the resultant signal waveform may change in a wavy form. The graph in FIG. 24 shows an example of such a waveform.

Referring to FIG. 24, the fuel-air ratio is detected on the lean side and is therefore determined to be in the falling state before timing F. Therefore, −1 is stored in the "state" flag, and a falling time signal (which is indicated by a two-dot chain line in FIG. 24 and which coincide with the reference signal (not shown) because RichTimeConstant=0) calculated using the transition rate LeanTimeConstant is output as the second intermediate signal (voltage Vint2). On and after the timing F when it is detected that the fuel-air ratio has been changed to the rich side, the fuel-air ratio is determined to be in the rising state, and the "state" flag becomes 1. Therefore, a rising time signal (indicated by a chain line in FIG. 24) calculated using the transition rate RichTimeConstant is output as the second intermediate signal (voltage Vint2). At the timing F, the voltage Vint2 of the second intermediate signal in the falling state is higher than the voltage Vint2 of the second intermediate signal in the rising state. A second intermediate signal (voltage Vint2) output as a combination of those signals draws a curve in which the voltage of the signal significantly lower than what it should be (as indicated by the arrow in FIG. 24) at the timing F when the voltage should increase conversely because the signal is in a rising state, the voltage increasing thereafter.

The first overshoot check process corrects any decrease in the voltage from the value at the timing F which occurs after the timing F in spite of the fact that the voltage is in the rising state. A similar correction is also made when the fuel-air ratio is changed from the rich side to the lean side. Specifically, the voltage is corrected such that no temporary voltage drop occurs when the fuel-air ratio has been changed from the lean side to the rich side and the voltage of the reference signal is therefore rising and such that no temporary voltage increase occurs when the fuel-air ratio has been changed from the rich side to the lean side and the voltage of the reference signal is therefore falling. Referring to the specific example shown in FIG. 24, the value of the voltage Vint2 in the rising state immediately before (1 ms before) the timing F is saved as the correction value Vbase, and a correction is made by substituting the correction value Vbase for the voltage Vint2 in the rising state during the period between the timing F and timing G until the value of the voltage Vint2 agrees with the correction value Vbase. As a result, in the example shown in FIG. 25, a third intermediate signal (voltage Vint3) obtained by the first overshoot check process draws a curve (shown in a solid line in FIG. 25) in which a straight line representing a constant voltage (Vbase) is substituted during the period from the timing F up to the timing G.

In order to obtain the voltage Vint3 by correcting the voltage Vint2 as described above, the main routing shown in FIG. 5 calls a subroutine for a first overshoot check process (S10). At the first overshoot check process, as shown in FIG. 12, reference is first made to the value of the "state" flag obtained at the threshold check process to check whether the value is greater than 0 or not (S121). Referring to the graph shown in FIG. 24 by way of example, the fuel-air ratio is detected as being in the state after a change from the rich side to the lean side (decreasing state), and the "state" flag is −1 (S121: NO). Therefore, a subroutine for a response slow-do process is called (S123).

In the response slow-down process shown in FIG. 14, reference is made to the value of the flag prevState2 in which the value of the "state" flag indicating the previous (1 ms ago) state of transition of the fuel-air ratio is stored and saved to check whether the value is greater than 0 or not (S151). Since the flag prevState2 is −1 before the timing F (S151: NO), it is determined that the fuel-air ratio has been on the lean side at the previous and current detection and that no change has been made on the same, and the process then proceeds to step S155 directly. The value of "CheckFlag" is 0 before a change occurs in the state of the fuel-air ratio (the value of the "state" flag) (S155: NO), and the voltage Vint2 of the second intermediate signal is stored as the voltage Vint3 of the third intermediate signal as it is (S161). Then, the process returns to the subroutine for the first overshoot check process shown on FIG. 12. The value of the "state" flag is stored and saved in the prevState2 flag to use the value when the first overshoot check process is executed next time. Further, the voltage Vint2 of the second intermediate signal is stored and saved as voltage prevVint2 to use the value of the voltage Vint2 when the response characteristics processing is executed next time (S125), and the process returns to the main routine.

When the timing F (see FIG. 24) comes after the process of the main routine is repeated every millisecond, a change in the fuel-air ratio from the lean state to the rich state is detected, and 1 is stored in the "state" flag. Then, the first overshoot check process shown in FIG. 12 calls a subroutine for a response speed increasing process (S121: YES, S122).

At the response speed increasing process shown in FIG. 13, since the value of the prevState2 flag for storing the value of the "state" flag before the timing F (see FIG. 24) is −1 (S131: YES), it is determined that the state of the fuel-air ratio has been changed from the lean side to the rich side. The value of the voltage prevVint2, which is the previously (1 ms ago) calculated voltage Vint2 of the second intermediate signal in a falling state, is copied and stored as a correction value Vbase substituted for the value of the voltage Vint2 when a correction is required (S132). Further, 1 is stored in the "CheckFlag" (S133).

Next, since the "CheckFlag" is 1 at step S135 (S135: YES), it is determined that the value of the voltage Vint2 must be corrected, and it is checked whether the voltage Vint2 is smaller than the correction value Vbase or not (S136). At the timing F, since the value of the voltage Vint2 calculated using the transition rate RichTimeConstant is smaller than the correction value Vbase, the voltage Vint2 must be corrected (S136: YES). Then, the correction value Vbase is stored as the voltage Vint3 (S137), and the process returns to the subroutine for the first overshoot check process.

At the timing F and afterward, the "state" flag indicates 1 because the fuel-air ratio is on the rich side, and the subroutine for the response speed increasing process is continuously called at the first overshoot check process (S121: YES in FIG. 12). Since 1 is also stored as the "prevState2" flag when the rising state continues (S131: NO), the correction value Vbase is maintained at that stored when the response speed increasing process was executed at the timing F. Further, since 1 is kept stored in the "CheckFlag" when the rising state continues (S135: YES), the correction value Vbase is substituted for the voltage Vint2 (S136: YES) as seen in the period between the timing F and the timing G (see FIG. 24), and a voltage Vint3 approximated by a straight line as described above is obtained (see FIG. 25) (S137).

When time passes further to reach the timing G, since the value of the voltage Vint2 becomes equal to or greater than the correction value Vbase, the response speed increasing process shown in FIG. 13 proceeds from step S136 to S139 (S136: NO). Since there is no need for correcting the voltage Vint2, the voltage Vint2 is stored as the voltage Vint3 (S139), and 0 is stored in the "CheckFlag" (S140). Then, the process returns to the subroutine for the first overshoot check process.

At the timing G and afterward, since the fuel-air ratio is still on the rich side, both of the "state" and "prevState2" flags indicate 1. The subroutine for the response speed increasing process is continuously called at the first overshoot check process (S121: YES in FIG. 12). At the response speed increasing process, since the "CheckFlag" is 0, the voltage Vint2 is stored as the voltage Vint3 as it is (S131: NO, S135: NO, S141), and the process returns to the subroutine for the first overshoot check process.

FIG. 23 shows an example of a graph representing the third intermediate signal (voltage Vint3) generated as thus described. In FIG. 23, the reference signal (voltage Vin) is subjected to neither gain processing nor response characteristics processing associated with a change in the fuel-air ratio from the lean side to the rich side. FIG. 23 shows a comparison between a graph (indicated by the chain line in the figure) of a third intermediate signal (voltage Vint3) and a graph (indicated by a dotted line in the figure) of a reference signal (voltage Vin). The third intermediate signal is generated by executing the first overshoot check process on a second intermediate signal (voltage Vint2) generated when a change in the fuel-air ratio from the rich side to the lean side (this event corresponds to the section C-E in FIG. 19) is detected. The third intermediate signal calculated using the rich-lean transition rate LeanTimeConstant has deteriorated response characteristics, and it will be understood that a change in the voltage Vint3 of the signal from high potential to low potential takes longer time compared to a change in the voltage Vin of the reference signal from high potential to low potential. It will be also observed that the voltage Vint3 is corrected by the first overshoot check process to prevent a temporary change in the voltage from low potential to high potential from occurring during the change in the same from high potential to low potential.

The response slow-down process shown in FIG. 14 is a process which is in a symmetrical relationship with the response speed increasing process described above and shown in FIG. 13 and which is executed when the fuel-air ratio has been changed from the rich side to the lean side. Therefore, the processes at steps S131 to S141 of the response speed increasing process correspond to the processes at steps S151 to S161 of the response slow-down process, respectively. The processes are identical in contents to each other except that signs of inequality are reversed at steps S151 and S156. Specifically, as shown in FIG. 14, at timing when a change in the fuel-air ratio from the rich side to the lean side is detected based on a change in the reference signal (state=−1, prevState2=1) (S121: NO S123 (see FIG. 12), S151: YES), the voltage prevVint2 that is the voltage Vint2 saved previously (1 ms ago) is stored as the correction value Vbase (S152), and 1 is stored in "CheckFlag" (S153). When the value of the voltage Vint2 is greater than the correction value Vbase and a correction is therefore required (S155: YES, S156: YES), the correction value Vbase is stored as the voltage Vint3 to substitute the correction value Vbase for the voltage Vint2 (S157). The substitution of the correction value Vbase for the voltage Vint2 is maintained thereafter (S151: NO, S155: YES, S156: YES, S157). On and after timing when the correction value Vbase becomes equal to or smaller than the voltage Vint2 (S156: NO), since there is no need for correcting the voltage Vint2, the voltage Vint2 is stored as the voltage Vint3 (S159), and 0 is stored in the "CheckFlag" (S160). Since the fuel-air ratio thereafter stays on the lean side, both of the "state" and "prevState2" flags are −1 (S121: NO, S123(see FIG. 12), S151: NO), and the "CheckFlag" is 0 (S155: NO, S161). Therefore, the voltage Vint2 is stored as the voltage Vint3 as it is.

FIG. 22 shows an example of a graph representing the third intermediate signal (voltage Vint3) generated at this time. In FIG. 22, the reference signal (voltage Vin) is subjected to neither gain processing nor response characteristics processing associated with a change in the fuel-air ratio from the lean side to the rich side. FIG. 22 shows a comparison between a graph (indicated by the chain line in the figure) of a third intermediate signal (voltage Vint3) and a graph (indicated by a dotted line in the figure) of a reference signal (voltage Vin). The third intermediate signal is generated by executing the first overshoot check process on a second intermediate signal (voltage Vint2) generated when a change in the fuel-air ratio from the lean side to the rich side (this event corresponds to the section A-C in FIG. 19) is detected. The third intermediate signal calculated using the lean-rich transition rate RichTimeConstant has deteriorated response characteristics, and it will be understood that a change in the voltage Vint3 of the signal from low potential to high potential takes longer time compared to a change in the voltage Vin of the reference signal from low potential to high potential.

[Delaying Process]

When the first overshoot check process is terminated and the process returns to the main routine shown in FIG. 5, a subroutine for a delaying process is called (S11). The delaying process is a process of obtaining a fourth intermediate signal (voltage Vint4) or a fifth intermediate signal (voltage Vint5) by delaying the starting point of a change in the reference signal (voltage Vin), which is the third intermediate signal (voltage Vint3) obtained through response characteristics processing in the present embodiment, as a result of a change in the target fuel-air ratio from the lean side to the rich side or from the rich side to the lean side such that the intermediate signal will be output at timing delayed by an amount set as a lean-rich delay time RichDelayTime or a rich-lean delay time LeanDelayTime.

At the delaying process shown in FIG. 15, the voltage Vint3 of the third intermediate signal obtained through the response characteristics processing and the first overshoot check process is stored in the voltage prevVint3[0] (S171). As described above, prevVint3[i] (i=0, 1, 2, ..., 600) represents 601 storage areas for storing and saving values of the voltage Vint3 obtained during a period of 600 ms at maximum. Values of the voltage Vint3 from that obtained at the delaying process executed previously (1 ms ago) up to the value of the voltage Vint3 obtained at the 600th latest delaying process (executed 600 ms ago) are saved in storage areas associated therewith. The value of the voltage Vint3 obtained by the current delaying process is saved in the storage area prevVint3[0] as described above. The CPU 11 stores the voltage Vint3 of the reference signal (which is the third intermediate signal in the present embodiment) in the storage area prevVint3[0] at step S171 to have voltages stored in the storage areas prevVint3[i] in the order of acquisition at the processes in subsequent steps S175 to S179. The CPU 11 corresponds to the "reference signal storing unit" of the invention.

Next, reference is made to a lean-rich delay time RichDelayTime for delaying the starting point of a change in the reference signal as a result of a change in the target fuel-air ratio from the lean side to the rich side. The delay time RichDelayTime is a delay time which is set by a user in advance within a range from 0 to 600 ms. A value of the voltage Vint3 of the third intermediate signal saved [RichDelayTime] ms ago is read from a storage area specified by prevVint3[RichDelayTime]. The value is stored as a voltage Vint4 of a fourth intermediate signal that is output with a delay of [RichDelayTime] ms (S172) when a change in the exhaust gas fuel-air ratio from the lean side to the rich side or a rising state is detected. Similarly, reference is made to a rich-lean delay time LeanDelayTime to read a value of the voltage Vint3 of the third intermediate signal saved [LeanDelayTime] ms ago from a storage area specified by prevVint3[LeanDelayTime]. The value is stored as a voltage Vint5 of a fifth intermediate signal that is output with a delay of [LeanDelayTime] ms (S173) when a change in the exhaust gas fuel-air ratio from the rich side to the lean side or a falling state is detected. As will be detailed later, the fourth intermediate signal is selected as a deterioration signal output by the sensor simulator 1 when it is detected that a change in the fuel-air ratio from the lean side to the rich side has resulted in a change in the reference signal. Similarly, the fifth intermediate signal is selected as a deterioration signal output by the sensor simulator 1 when it is detected that a change in the fuel-air ratio from the rich side to the lean side has resulted in a change in the reference signal. At steps S172 and S173, the CPU 11 reads voltages Vint3 of the reference signal (which is the third intermediate signal in the present embodiment) obtained [RichDelayTime] ms ago and [LeanDelayTime] ms ago from prevVint3[RichDelayTime] and prevVint3[LeanDelayTime] and stores the voltages as the voltage Vint4 of the fourth intermediate signal and the voltage Vint5 of the fifth intermediate signal, respectively to output them as deterioration signals. The CPU 11 therefore corresponds to the "signal delay generation unit" of the invention.

At subsequent steps S175 to S179, processes of updating the storage areas prevVint3[i] are executed to allow them to be used when the next delaying process is executed. First, 600 is stored as the variable i at step S175 (S175). A process is then executed to store the value of the storage area prevVint3[i−1 (599)] in the storage area prevVint3[i(600)] (S176). Then, the variable i is decremented to 599 (S177), and the process returns to step S175 because i≧1 is satisfied (S179: YES). Then, a process of storing the value of the storage area prevVint3[i−1(598)] in the storage area prevVint3[i(599)] is similarly executed. The series of processes is continued until the value of the variable i becomes smaller than 1 (S179: NO), and the values which have been in the storage areas prevVint3[599] to prevVint3[0] are stored in the storage areas prevVint3[600] to prevVint3[1], respectively, to overwrite and update the latter storage areas. The process then returns to the main routine.

[Second Overshoot Check Process]

When the fuel-air ratio is changed, the fifth intermediate signal or the fourth intermediate signal is selected as a deterioration signal instead of the fourth intermediate signal or the fifth intermediate signal which has been selected prior to the change. The switching from the fourth intermediate signal to the fifth intermediate signal or from the fifth intermediate signal to the fourth intermediate signal takes place at the timing when a change in the reference signal takes place as a result of the change in the fuel-air ratio is detected. As described above, the voltage Vint4 of the fourth intermediate signal or the voltage Vint5 of the fifth intermediate signal may have already started changing (increasing or attenuating) significantly at that timing. For this reason, the direction of change in the voltage Vout of the deterioration signal may temporarily be reversed at the above-described timing. For example, the voltage Vout of the deterioration signal changes from high potential to low potential when the target fuel-air ratio is changed from the rich side to the lean side. However, a change from low potential to high potential may take place at the above-described timing, and the resultant signal waveform may have a change in the form of a wave. The graph in FIG. 28 represents an example of such a phenomenon.

Referring to FIG. 28, the fuel-air ratio is detected on the rich side and is determined to be in the rising state before timing H. Therefore, 1 is stored in the "state" flag, and a fourth intermediate signal (voltage Vint4) indicated by a chain line is selected as a signal to be output by a deterioration signal (the signal coincides with the reference signal because RichDelayTime=0 in the example shown in FIG. 28). At timing H when a change from the rich side to the lean side is detected, the fuel-air ratio is determined to be in the falling state, and the "state" flag becomes −1. Therefore, a fifth intermediate signal indicated by a two-dot chain line is substituted for the fourth intermediate signal as to provide a signal output as a deterioration signal. At the timing H, the voltage Vint4 of the fourth intermediate signal is lower than 0.9 V. That is, the voltage has started to change from about 0.9 V which represents a stable state of the fuel-air ratio on the rich side to about 0.05 V which represents a stable state of the fuel-air ratio on the lean side. On the contrary, the voltage Vint5 of the fifth intermediate signal at the timing H is the voltage Vint3 of the third intermediate signal detected [LeanDelayTime] ms ago (which is the voltage Vin of the reference signal in the example shown in FIG. 28). More specifically, the voltage Vint5 is about 0.9 V before the rich-lean delay time which corresponds to the period from the timing H up to timing I in FIG. 28. As a result, a combination of the fourth intermediate signal and the fifth intermediate signal shown in FIG. 28 is output as a deterioration signal. The signal draws a curve in which the voltage is significantly higher than what it should be (as indicated by the arrow) at the timing H when the voltage should be in a falling state and should therefore be changing downward, the voltage starting to decrease thereafter.

The second overshoot check process corrects any increase in the voltage from the value at the timing H which occurs after the timing H in spite of the fact that the voltage is in the falling state. A similar correction is also made when the fuel-air ratio is changed from the lean side to the rich side. Specifically, the voltage is corrected such that no temporary voltage drop occurs when the fuel-air ratio has been changed from the lean side to the rich side and the voltage of the reference signal is therefore rising and such that no temporary voltage increase occurs when the fuel-air ratio has been changed from the rich side to the lean side and the voltage of the reference signal is therefore falling. Referring to the specific example shown in FIG. 28, the value of the voltage Vint5 immediately before (1 ms before) the timing H is saved as the correction value Vbase, and a correction is made by substituting the correction value Vbase for the voltage Vint4 during the period between the timing H and timing I until the value of the voltage Vint4 agrees with the correction value Vbase. As a result in the example shown in FIG. 29, a deterioration signal (voltage Vout) obtained by the second overshoot check process draws a curve (indicated by the solid line in FIG. 29) in which a straight line representing a constant voltage (Vbase) is substituted during the period from the timing H up to the timing I.

In order to obtain a deterioration signal by correcting a fourth intermediate signal and a fifth intermediate signal which have been subjected to the delaying process as described above, the main routine shown in FIG. 5 calls a subroutine for a second overshoot check process. At the second overshoot check process, as shown in FIG. 16, reference is first made to the value of the "state" flag obtained at the threshold check process to check whether the value is greater than 0 or not (S181). Referring to the graph shown in FIG. 28 by way of example, before the timing H comes, it is determined the fuel-air ratio has been changed from the lean side to the rich side (rising state), and the "state" flag is 1 (S181: YES). Therefore, a subroutine for a delay increasing process is called (S182). The CPU 11 selects a delay increasing process or delay decreasing process according to the value of the "state" flag such that the fourth intermediate signal or fifth intermediate signal will be generated as a deterioration signal. The CPU 11 therefore corresponds to the "deterioration signal selection generation unit" of the invention.

At the delay increasing process shown in FIG. 17, reference is made to the value of the flag prevState3 in which the value of the "state" flag indicating the state of transition of the fuel-air ratio detected previously (1 ms ago) is stored and saved, and it is checked whether the value is smaller than 0 or not (S191). Since the value in the flag prevState3 is 1 before the timing Hi comes (S191: NO), it is determined that the fuel-air ratio has been on the rich side at the previous and current detection and that not change has been made on the same, and the process directly proceeds to step S195. Before a change occurs in the state of the fuel-air ratio (the value in the "state" flag), the value in the "CheckFlag" is 0 (S195: NO) indicating the rising state in which the "state" flag is 1. Therefore, the fourth intermediate signal is selected as a deterioration signal, and the voltage Vint4 is stored as the voltage Vout (S201). Then, the process returns to the subroutine for the second overshoot check process shown in FIG. 16. Further, the values of the "state" flag, voltage Vint4, and voltage Vint5 are stored and saved as the state prevState3, the voltage prevVint4, and the voltage prevVint5, respectively (S185), and the process returns to the main routine.

When the processes at the main routine are repeated every millisecond and the timing H comes (see FIG. 28), it is determined that the fuel-air ratio has been changed from the rich state to the lean state, and −1 is stored in the "state" flag. Then, a subroutine for a delay decreasing process is called at the second overshoot check process shown in FIG. 16 (S181: NO, S183).

At the delay decreasing process shown in FIG. 18, since the flag prevState3 storing the value of the "state" flag before the timing H (see FIG. 28) has a value of 1 (S211: YES), it is determined that the state of the fuel-air ratio has been changed from rich to lean. Then, the value of the voltage prevVint4 that is the voltage Vint4 of the fourth intermediate signal selected and saved previously (1 ms ago) is copied and stored as the correction value Vbase which will be substituted for the voltage Vint5 when the same voltage is to be corrected (S212). And, 1 is stored in the "CheckFlag" (S213) The CPU 11 copies and stores the previous voltage prevVint4 of the fourth intermediate signal as a correction value Vbase corresponding to the "rich-lean holding signal" of the invention at step S212. The CPU 11 also copies and stores the previous voltage prevVint5 of the fifth intermediate signal as a correction value Vbase corresponding to the "lean-rich holding signal" of the invention at step S192 to be described later. The CPU 11 therefore corresponds to the "holding signal storing unit" of the invention.

At step S215, since the "CheckFlag" is 1 (S215: YES), it is checked whether the voltage Vint5 is greater than the correction value Vbase or not in order to determine whether to correct the value of the voltage Vint5 (S216). Since the value of the voltage Vint5 at the timing H (see FIG. 28) is greater than the correction value Vbase, the voltage Vint5 must be corrected (S216: YES). Then, the correction value Vbase is stored as the voltage Vout of a deterioration signal that is to be finally output (S217), and the process returns to the subroutine for the second overshoot check process.

On and after the timing H, the "state" flag shows −1 because the fuel-air ratio is on the lean side, and the subroutine for the delay decreasing process is continuously called at the second overshoot check process (S181: YES in FIG. 16). Since −1 is also stored in the flag prevState3 when the failing state continues (S211: NO), the correction value Vbase is maintained at the value which has been stored at the delay decreasing process at the timing H. Further, since 1 is kept stored in the "CheckFlag" (S215: YES), the correction value Vbase is substituted for the voltage Vint5 (see FIG. 28) as seen in the period from the timing H until the timing I (S216: YES) to obtain a voltage Vout which is approximated by a straight line in a way similar to that described above (S217). The CPU 11 stores the correction value Vbase saved at step S212 as the voltage Vout of the deterioration signal to be output at step S217 and similarly stores the correction value Vbase saved at step S192 as the voltage Vout of the deterioration signal to be output. The CPU 11 therefore corresponds to the "holding signal output unit" of the invention.

When time passes to reach the timing I, since the value of the voltage Vint5 is equal to or smaller than the correction value Vbase, the delay decreasing process shown in FIG. 18 proceeds from step S216 to step S219 (S216: NO). Since there is no need for correcting the voltage Vint5, the voltage Vint5 is stored as the voltage Vout (S219), and 0 is stored in the "CheckFlag" (S220). Then, the process returns to the subroutine for the second overshoot check process.

Since the fuel-air ratio stays on the lean side after on and after the timing I, both of the flags "state" and "prevState3" are −1. Then, the subroutine for the delay decreasing process is continuously called at the second overshoot check process (S181 NO in FIG. 16). At the delay decreasing process, since the "CheckFlag" is 0, the voltage Vint5 is stored as the voltage Vout as it is (S211: NO, S215: NO, S221), and the process returns to the subroutine for the second overshoot check process. The CPU 11 copies and stores the voltage Vint5 as the voltage Vout such that the fifth intermediate signal will be output as a deterioration signal at steps S219 and S221. The CPU 11 therefore corresponds to the "rich-lean signal delay output unit".

FIG. 27 shows an example of a graph representing a deterioration signal (voltage Vout) generated as thus described. In FIG. 27, the reference signal (voltage Vin) is not subjected to any of gain processing, response characteristics processing, and a delaying process associated with a change in the target fuel-air ratio from the lean side to the rich side. FIG. 27 shows a comparison between a graph (indicated by the chain line in the figure) of a deterioration signal (voltage Vout) and a graph (indicated by a dotted line in the figure) of a reference signal (voltage Vin). The deterioration signal is generated by executing the second overshoot check process on a fifth intermediate signal selected when a change in the fuel-air ratio from the rich side to the lean side (this event corresponds to the section C-E in FIG. 19) is detected. It will be understood that the deterioration signal (voltage Vout) is output with a delay equivalent to the rich-lean delay time LeanDelayTime when the voltage Vin of the reference signal changes from the high potential to low potential. It will be also observed that the voltage Vout is corrected by the second overshoot check process to prevent a temporary change in the voltage from high potential to low potential from occurring during the change in the same from low potential to high potential.

The delay increasing process shown in FIG. 17 is a process which is in a symmetrical relationship with the delay decreasing process described above and shown in FIG. 18 and which is executed when the fuel-air ratio has been changed from the lean side to the rich side. Therefore, the processes at steps S211 to S221 of the delay decreasing process correspond to the processes at steps S191 to S201 of the delay increasing process, respectively.

The processes are executed to select the fourth intermediate signal (voltage Vint4) as the deterioration signal to be output (voltage Vout). Specifically, as shown in FIG. 17, at timing when a change in the fuel-air ratio from the lean side to the rich side is detected based on a change in the reference signal (state=1, prevState3=−1) (S181: YES, S182 (see FIG. 16), S191: YES), the voltage prevVint5 that is the voltage Vint5 selected and saved previously (1 ms ago) is stored as the correction value Vbase (S192), and 1 is stored in "CheckFlag" (S193). When the value of the voltage Vint4 is smaller than the correction value Vbase and a correction is therefore required (S195: YES, S196: YES), the correction value Vbase substituted for the voltage Vint4 is stored as the voltage Vout of the deterioration signal (S197). The substitution of the correction value Vbase for the voltage Vint4 is continued thereafter (S191: NO, S195: YES, S196: YES, S197). On and after timing when the correction value Vbase becomes equal to or greater than the voltage Vint4 (S196: NO), since there is no need for correcting the voltage Vint4, the voltage Vint4 is stored as the voltage Vout (S199), and 0 is stored in the "CheckFlag" (S200). Since the fuel-air ratio thereafter stays on the rich side, both of the "state" and "prevState3" flags are 1 (S181. YES, S182 (see FIG. 16), S191: NO), and the "CheckFlag" is 0. Therefore, the voltage Vint4 is stored as the voltage Vout as it is (S195: NO, S201). The CPU 11 which copies and stores the voltage Vint4 as the voltage Vout such that the fourth intermediate signal will be output as a deterioration signal at steps S199 and S201 corresponds to the "lean-rich signal delay output unit" of the invention.

FIG. 26 shows an example of a graph representing a deterioration signal (voltage Vout) generated at this time. In FIG. 26, the reference signal (voltage Vin) is not subjected to any of gain processing, response characteristics processing, and a delaying process associated with a change in the target fuel-air ratio from the rich side to the lean side. FIG. 26 shows a comparison between a graph (indicated by the chain line in the figure) of a deterioration signal (voltage Vout) and a graph (indicated by a dotted line in the figure) of a reference signal (voltage Vin). The deterioration signal is generated by executing the second overshoot check process on a fourth intermediate signal selected when a change in the fuel-air ratio from the lean side to the rich side (this event corresponds to the section A-C in FIG. 19) is detected. It will be understood that the deterioration signal (voltage Vout) is output with a delay equivalent to the lean-rich delay time RichDelayTime when the voltage Vin of the reference signal changes from the low potential to high potential. It will be also observed that the voltage Vout is corrected by the second overshoot check process to prevent a temporary change in the voltage from high potential to low potential from occurring during the change in the same from low potential to high potential.

As described above, the deterioration signal generation program is executed to perform gain processing, response characteristics processing, and delaying process on a reference signal (voltage Vin), whereby a deterioration signal (voltage Vout) is generated. FIG. 30 shows a graph representing the deterioration signal (Vout) (indicated by a chain line in the figure). The deterioration signal has a signal waveform in which voltage changes are slower than those in the graph representing the reference signal (indicated by a dotted line in the figure) although the voltage changes in accordance with changes in a target fuel-air ratio. In any of the gain processing, response characteristics processing, and delaying process, different parameters may be used when the fuel-air ratio is on the rich side and when it is on the lean side to allow the contents of the processes on a signal to be set differently. It is therefore possible to simulate various states of deterioration of a reference signal.

The invention is not limited to the above-described embodiment and may be modified in various ways. For example, an input/output interface such as a USB or RS232C interface may be provided to allow connection with a personal computer using an appropriate cable, which allows set values to be input, displayed, and checked. A reference signal from the reference sensor 2 or a deterioration signal generated may be output to the personal computer through the input/output interface to allow an output waveform of the same to be generated and monitored on the personal computer. Obviously, the output waveform may alternatively be displayed on the display unit 80.

A plurality of combinations of set values may be stored in the set value storage area 121 of the EEPROM 12. Specifically, set values adapted to each sensor to be used as the reference sensor 2, e.g., a fuel-air ratio sensor or a NOx sensor can be thus read, which makes it possible to eliminate time and labor required for re-entering set values each time the sensor to be connected is switched. Obviously, a common ROM mat be used instead of the EEPROM 12, and such combinations of set values may be saved in the same as preset values.

In the present embodiment, the processing blocks shown in FIG. 4, i.e., the gain processing block, response characteristics processing block, and the delaying processing block are executed in the order listed. The blocks may be executed independently of each other and may be executed in any order. However, the rise and fall detection block may be executed prior to the response characteristics processing block and the delaying process block.

The seven variables which can be set by a user (RichGain, LeanGain, GainThreshold, RichTimeConstant, LeanTimeConstant, RichDelayTime, and LeanDelayTime) are copied from the set value storage area 121 of the EEPROM 12 to the variable storage area 132 of the RAM 13 at the initialization process at step S1, and the values stored in the variable storage area 132 are referred to at the subsequent processes. Alternatively, reference may be made to the value stored in the set value storage area 121 for those seven variables. Thus, when a user has made a change in any set value during the execution of the deterioration signal generation program, results of the change can be immediately reflected in the deterioration signal generated.

In the present embodiment, a deterioration signal is generated from a reference signal on a software basis by executing the deterioration signal generation program. Alternatively, a deterioration signal may be generated by fabricating an analog or digital hardware circuit constituting a logic circuit.

The invention can be applied to deterioration signal generation device capable of simulating deterioration signals generated by various sensors such as universal fuel-air ratio sensors and NOx sensors in deteriorated states of the sensors.

This application is based on Japanese Patent Application JP 2006-143453, filed May 24, 2006, the entire content of which is hereby incorporated by reference, the same as if set forth at length.

What is claimed is:

1. A deterioration signal generation device for a gas sensor for simulating a deterioration signal output by a gas sensor in a deteriorated state, the gas sensor detecting the fuel-air ratio of exhaust gas from an internal combustion engine based on the concentration of particular components in the exhaust gas, the deterioration signal generation device comprising:
    a reference signal acquisition unit which is connected to a reference sensor identical in configuration to the gas sensor for outputting a reference signal for generating the deterioration signal, the reference signal being associated with the concentration of the particular component in the exhaust gas, and which acquires the reference signal at constant time intervals;
    a reference signal storing unit for storing the reference signals acquired by the reference signal acquisition unit in the order of acquisition;
    a delay time setting unit for setting a delay time for outputting the reference signal while delaying the starting point of a change in the signal as a result of a change in a target fuel-air ratio of a mixture supplied to the internal combustion engine; and
    a signal delay generation unit for generating the reference signal stored in the reference signal storing unit at a time preceding the current opportunity for acquisition a number of times corresponding to the delay time set by the delay time setting unit.

2. The deterioration signal generation device for a gas sensor according to claim 1, wherein
    the delay time setting unit is configured to be able to separately set a rich-lean delay time for delaying the start of a change in the reference signal in the case of a change from the target fuel-air ratio from a rich side to a lean side and a lean-rich delay time for delaying the start of a change in the reference signal in the case of a change in the target fuel-air ratio from the lean side to the rich side; and the signal delay generation unit comprises:
    a rich-lean signal delay output unit for outputting the reference signal stored in the reference signal storing unit at a time preceding the current opportunity for acquisition a number of times corresponding to the rich-lean delay time;
    a lean-rich signal delay output unit for outputting the reference signal stored in the reference signal storing unit at a time preceding the current opportunity for acquisition a number of times corresponding to the lean-rich delay time; and
    a deterioration signal selection generation unit for generating the reference signal output from the rich-lean signal delay output unit as the deterioration signal when the value of the reference signal acquired by the reference signal acquisition unit has changed from the rich side to the lean side and generating the reference signal output from the lean-rich signal delay output unit as the deterioration signal when the value of the reference signal acquired by the reference signal acquisition unit has changed from the lean side to the rich side.

3. The deterioration signal generation device for a gas sensor according to claim 2, comprising:
    a fuel-air ratio change starting point detection unit for detecting a rich-lean change starting point as the starting point of a change in the reference signal as a result of a change from the target fuel-air ratio from the rich side to the lean side and a lean-rich change starting point as the starting point of a change in the reference signal as a result of a change in the target fuel-air ratio from the lean side to the rich side based on a plurality of the reference signals acquired by the reference signal acquisition unit, wherein the deterioration signal selection generation unit performs switching at the rich-lean change starting point such that the reference signal output from the rich-lean signal delay output unit will be generated as the deterioration signal and performs switching at the lean-rich change starting point such that the reference signal output from the lean-rich signal delay output unit will be generated as the deterioration signal.

4. The deterioration signal generation device for a gas sensor according to claim 3, wherein the fuel-air ratio change starting point detection unit executes a process of differentiating the reference signal and detects a differential of the reference signal exceeding a threshold for a change in the target fuel-air ratio from the rich side to the lean side as the rich-lean change starting point and a differential exceeding a threshold for a change in the target fuel-air ratio from the lean side to the rich side as the lean-rich change starting point.

5. The deterioration signal generation device for a gas sensor according to claim 1, comprising:

a gain factor setting unit for setting a gain factor for outputting the reference signal with the gain of the same changed; and a gain changing unit for changing the gain of the reference signal by multiplying the reference signal by the gain factor set by the gain factor setting unit.

6. The deterioration signal generation device for a gas sensor according to claim 5, wherein:

the gain factor setting unit is configured to be able to separately set a lean gain factor for changing the gain of the reference signal when the value of the reference signal is leaner than a predetermined threshold and a rich gain factor for changing the gain of the reference signal when the value of the reference signal is richer than the predetermined threshold; and the gain changing unit multiplies the reference signal by the lean gain factor when it is determined that the value of the reference signal is leaner than the predetermined threshold and multiplies the reference signal by the rich gain factor when it is determined that the value of the reference signal is richer than the predetermined threshold.

7. The deterioration signal generation device for a gas sensor according to claim 1, comprising:

a transition rate setting unit for setting a transition rate for outputting the reference signal with response characteristics of the signal changed, the response characteristics changing as the target fuel-air ratio changes; and a transition time changing unit for changing the response characteristics of the reference signal by multiplying the reference signal by the transition rate set by the transition rate setting unit.

8. The deterioration signal generation device for a gas sensor according to claim 7, wherein:

the transition rate setting unit is configured to be able to separately set a rich-lean transition rate for changing the response characteristics of the reference signal in the case of a change in the target fuel-air ratio from the rich side to the lean side and a lean-rich transition rate for changing the response characteristics of the reference signal in the case of a change in the target fuel-air ratio from the lean side to the rich side; and the transition time changing unit multiplies the reference signal by the rich-lean transition rate when the value of the reference signal acquired by the reference signal acquisition unit changes from the rich side to the lean side and multiplies the reference signal by the lean-rich transition rate when the value of the reference signal acquired by the reference signal acquisition unit changes from the lean side to the rich side.

9. The deterioration signal generation device for a gas sensor according to claim 3, comprising:

a holding signal storing unit for storing the deterioration signal generated at the rich-lean change starting point as a rich-lean holding signal and storing the deterioration signal generated at the lean-rich change starting point as a lean-rich holding signal; and a holding signal output unit for outputting the rich-lean holding signal as the deterioration signal when the deterioration signal generated after the rich-lean change starting point has a value greater than that of the rich-lean holding signal, the holding signal being output until the deterioration signal generated after the rich-lean change starting point becomes a value equal to or smaller than that of the rich-lean holding signal and for outputting the lean-rich holding signal as the deterioration signal when the deterioration signal generated after the lean-rich change starting point has a value smaller than that of the lean-rich holding signal, the holding signal being output until the deterioration signal generated after the lean-rich change starting point becomes a value equal to or greater than that of the lean-rich holding signal.

* * * * *